(12) United States Patent
Jiao et al.

(10) Patent No.: US 11,046,652 B2
(45) Date of Patent: Jun. 29, 2021

(54) HYDROXAMIC ACIDS COMPRISING PYRAZOLE MOIETY AND USES THEREOF

(71) Applicant: HAWAII BIOTECH, INC., Honolulu, HI (US)

(72) Inventors: Guan-Sheng Jiao, Aiea, HI (US); Alan T. Johnson, Kaneohe, HI (US); Sean O'Malley, Honolulu, HI (US); Seong Jin Kim, Honolulu, HI (US)

(73) Assignee: HAWAII BIOTECH, INC., Honolulu, HI (US)

( * ) Notice: Subject to any disclaimer, the term of this patent is extended or adjusted under 35 U.S.C. 154(b) by 0 days.

(21) Appl. No.: 16/911,075

(22) Filed: Jun. 24, 2020

(65) Prior Publication Data

US 2020/0399223 A1 Dec. 24, 2020

Related U.S. Application Data

(60) Provisional application No. 62/865,863, filed on Jun. 24, 2019.

(51) Int. Cl.
*C07D 231/12* (2006.01)

(52) U.S. Cl.
CPC .................................. *C07D 231/12* (2013.01)

(58) Field of Classification Search
CPC .................................................... C07D 231/12
See application file for complete search history.

(56) References Cited

FOREIGN PATENT DOCUMENTS

| WO | 92-16200 A1 | 10/1992 |
|---|---|---|
| WO | 2016-168483 A1 | 10/2016 |

OTHER PUBLICATIONS

No new references.*

Patent Cooperation Treaty, International Search Report and Written Opinion issued in PCT/US2020/039381, Oct. 19, 2020, pp. 1-13.
Boldt, G. E. et al., "Identification of a potent botulinum neurotoxin A protease inhibitor using in situ lead identification chemistry", Org Lett., pp. 1729-1732, Apr. 13, 2006, vol. 8(8).
Deprez-Poulain, R. et al., "Catalytic site inhibition of insulin-degrading enzyme by a small molecule induces glucose intolerance in mice", Nature Communications, Sep. 23, 2015, pp. 1-13, vol. 6 (Article No. 8250).
Fieulaine, S. et al., "A unique peptide deformylase platform to rationally design and challenge novel active compounds", Scientific Reports, Oct. 20, 2016, pp. 1-15, vol. 6 (Article No. 35429).

* cited by examiner

*Primary Examiner* — Shawquia Jackson
(74) *Attorney, Agent, or Firm* — Pillsbury Winthrop Shaw Pittman LLP

(57) ABSTRACT

Compounds of Formula I are provided:

$R^1$ is $-OR^5$, m is an integer from 0 to 5, n is an integer from 0 to 2, each $R^2$ is independently selected from hydrogen, halogen, and alkyl, $R^3$ is selected from hydrogen, alkyl, cycloalkyl, aryl, hydroxyalkyl, alkoxyalkyl, aryloxyalkyl, aralkyloxyalkyl, aralkyl, alkylaminoalkyl, dialkylaminoalkyl, aralkylaminoalkyl, and heterocycloalkyl, $R^5$ is an alkyl, each $R^4$ is independently hydrogen or alkyl, and each of $R^2$, $R^3$, $R^4$, and $R^5$ is independently optionally substituted. Compounds of Formula I are included in pharmaceutical compositions for the treatment of a subject exposed to a *botulinum* toxin.

33 Claims, No Drawings

Specification includes a Sequence Listing.

HYDROXAMIC ACIDS COMPRISING PYRAZOLE MOIETY AND USES THEREOF

STATEMENT OF RELATED APPLICATIONS

This application claims priority to U.S. Provisional Patent Application No. 62/865,863, filed Jun. 24, 2019, the contents of which are incorporated herein by reference in its entirety.

STATEMENT OF GOVERNMENT SPONSORSHIP

This invention was made with government support under HDTRA1-13-C-0007 awarded by the Department of Defense, Defense Threat Reduction Agency. The government has certain rights in the invention.

SEQUENCE LISTING

The instant application contains a Sequence Listing which has been submitted electronically in ASCII format and is hereby incorporated by reference in its entirety. Said ASCII copy, created on Jun. 23, 2020, is named HIB-0513534_ST25.txt and is 4,796 bytes in size.

INTRODUCTION

The present disclosure relates to compounds developed to treat exposure to toxins, such as Botulinum neurotoxin (BoNT). In particular, the present disclosure relates to hydroxamic acid compounds comprising a pyrazole moiety that serve as inhibitors of toxins, such as BoNT.

Botulinum neurotoxin A (BoNT/A), in particular, has an LD50 of 1 ng/kg i.v. in mammals (100 ng/kg inhalational, 14 ng/kg oral) (Burnett et al. *Nat. Rev. Drug Disc.* 4(4):281-296 (2005); Wein et al. *Proc. Natl. Acad. Sci. U.S.A.* 102(28): 9984-9989 (2005)). Its ease of production, transport, and delivery make it a significant threat as a biological warfare and bioterrorism weapon (Glik et al. *Biosecur. Bioterror.* 2(3):216-223 (2004). Military programs to develop BoNT as a biological warfare agent in multiple nations have been documented (Arnon et al. *J. Am. Med. Assoc.* 285(8): 1059-1070 (2001); Noah et al. *Emerg. Med. Clin. North Am.* 20(2): 255-71 (2002)). Recently, the growth of international manufacturing of BoNT/A for legitimate medical use has significantly increased the risk of easy access to toxin in quantity through criminal means. BoNT/A is therefore a Pharmaceutical-Based Agent; a terrorist organization or rogue state need not develop sophisticated technical capabilities for toxin production on its own, but could acquire commercially prepared toxin via the black market (Coleman, K. D. and R. A. Zilinskas, *The Security Threat from Producers of Counterfeit Botulinum Toxin,* 2011, James Martin Center for Nonproliferative Studies: Monterey). The current acceleration of synthetic biology techniques also increases the likelihood that a novel infectious agent (an Advanced Agent) could be engineered to deliver BoNT/A, thereby circumventing clearance-based countermeasures for the toxin (National Academies of Sciences, Engineering, and Medicine, *A Proposed Framework for Identifying Potential Biodefense Vulnerabilities Posed by Synthetic Biology: Interim Report,* 2017, the National Academies Press: Washington, D.C., https://doi.org/10.17226/24832). Development and stockpiling of a BoNT inhibitor small molecule therapeutic drug is a priority of the Joint Science and Technology Office-Chemical and Biological Defense/Defense Threat Reduction Agency for warfighter protection. BoNT is a CDC/NIAID Category A Biodefense Pathogen, one of twelve Top Priority Biological Threats for which the Department of Homeland Security has completed full Material Threat Determinations and Population Threat Assessments.

SUMMARY

In some aspects, there are provided compounds of formula I:

I wherein $R^1$ is —$OR^5$;
m is an integer from 0 to 5;
n is an integer from 0 to 2;
each $R^2$ is independently selected from the group consisting of hydrogen, halogen, and alkyl;
$R^3$ is selected from the group consisting of hydrogen, alkyl, cycloalkyl aryl, hydroxyalkyl, alkoxyalkyl, aryloxyalkyl, aralkyloxyalkyl, aralkyl, alkylaminoalkyl, dialkylaminoalkyl, aralkylaminoalkyl, and heterocycloalkyl,
each $R^4$ is independently hydrogen or alkyl;
$R^5$ is an alkyl; and
each of $R^2$, $R^3$, $R^4$, and $R^5$ being independently optionally substituted.

In some aspects, there are provided compounds of formula II:

II wherein $R^1$ is —$OR^5$;
m is an integer from 0 to 5;
n is an integer from 0 to 2;
each $R^2$ is independently selected from the group consisting of hydrogen, halogen, and alkyl;
$R^3$ is selected from the group consisting of hydrogen, alkyl, cycloalkyl aryl, hydroxyalkyl, alkoxyalkyl, aryloxyalkyl, aralkyloxyalkyl, aralkyl, alkylaminoalkyl, dialkylaminoalkyl, aralkylaminoalkyl, and heterocycloalkyl,
each $R^4$ is independently hydrogen or alkyl;
$R^5$ is an alkyl; and
each of $R^2$, $R^3$, $R^4$, and $R^5$ being independently optionally substituted.

In some aspects, there are provided compounds of formula III:

$$\text{III}$$

[Structure: a compound showing HO-NH-C(=O)-CH₂-CH(R¹)-CH(-CH₂-phenyl(R²)ₘ)-pyrazole(R⁴)ₙ-N-R³]

wherein R¹ is —OR⁵;
m is an integer from 0 to 5;
n is an integer from 0 to 2;
each R² is independently selected from the group consisting of hydrogen, halogen, and alkyl;
R³ is selected from the group consisting of hydrogen, alkyl, cycloalkyl aryl, hydroxyalkyl, alkoxyalkyl, aryloxyalkyl, aralkyloxyalkyl, aralkyl, alkylaminoalkyl, dialkylaminoalkyl, aralkylaminoalkyl, and heterocycloalkyl,
each R⁴ is independently hydrogen or alkyl;
R⁵ is an alkyl; and
each of R², R³, R⁴, and R⁵ being independently optionally substituted.

The aforementioned compounds may be formulated in pharmaceutical compositions comprising the compound along with a pharmaceutically acceptable carrier.

The aforementioned compositions may be used in methods of treating a subject exposed to a *botulinum* toxin comprising administering to the subject the pharmaceutical composition.

DETAILED DESCRIPTION

The *botulinum* neurotoxins (BoNTs) have been indicated to inhibit acetylcholine release at the neuromuscular junction and other peripheral cholinergic sites (Arnon et al. supra; Poulain et al. *The Botulinum J.* 1(1):14-87 (2008)). At least seven serologically distinct BoNT proteins (types /A through /G) are produced by different strains of the anaerobic bacterium *Clostridium botulinum*; it has been indicated that type /A is the most lethal protein toxin. Symptoms of BoNT intoxication can include difficulty swallowing, impaired vision, muscle weakness, and death due to respiratory failure (MacDonald et al. *J. Am. Med. Assoc.* 253: 1275-1278 (1985)). Exposure to toxin in a bioterrorism scenario could occur through ingestion or inhalation (Park et al. *Infect. Immun.* 71(3): 1147-54 (2003)).

Without being bound by theory, it is postulated that the BoNTs exert their biological effects by a triphasic mechanism involving: 1) serotype-specific 'double-receptor' binding to sialic acid and protein receptors on the surface of motor nerve endings, 2) internalization of the toxin-receptor complex and translocation of proteolytic subunit LC into the cytoplasm, and 3) intraneuronal cleavage of proteins responsible for neurotransmitter release (Montal *Annu. Rev. Biochem.* 79:591-617 (2010)). The holotoxins consist of a heavy chain (HC, MW≈100 kD) that mediates receptor binding and internalization, and a zinc-metalloprotease light chain (LC, MW≈50 kD). The LCs are partially unfolded in the acidic endosome and translocated into the cytosol through a narrow HC channel. They may be phosphorylated and/or palmitoylated once inside the cell; these modifications may enable serotype-specific trafficking that could be responsible for the unique months-long persistence of serotype A (and to a lesser extent, B) (Dong et al. *Proc. Natl. Acad. Sci. U.S.A.* 101(41):14701-14706 (2004); Fernandez-Salas *Mov. Disord.* 19(8):523-534 (2004)). While the exact mechanism of persistence has not been fully elucidated, evasion of the ubiquitination-proteasome degradation pathway may be involved (Tsai et al. *Proc. Natl. Acad. Sci. U.S.A.* 107(38): 16554-16559 (2010)).

Light chain /A is believed to exert its intraneuronal effects by site-specific cleavage of SNAP-25 (25 kD synaptosomal associated protein), one of three proteins that form the complex that mediates fusion of carrier vesicles to target membranes (SNARE, soluble N-ethylmaleimide-sensitive fusion protein-attachment protein receptor). Disruption of the SNARE complex can prevent vesicle exocytosis, thus blocking neurotransmitter secretion. Each serotype of BoNT cleaves a SNARE protein at a unique site. The high cleavage specificity of the BoNTs is thought to be due to a complex substrate binding mechanism involving exosites (Montal 2010, supra).

Though there are significant differences in potency among serotypes, with /A being the most potent, a striking difference lies in the persistence of their effect. Recovery of paralyzed nerve endings takes 30-90 days (or more) after intoxication with serotype A, and a few weeks with type B, while the remaining serotypes have a much shorter duration (days or hours) (Adler et al. *Toxicon* 39(2-3):233-43 (2001); Foran et al. *Trends Mol. Med.* 9(7): 291-9 (2003)). Serotype A was selected as the initial target because of its potency and persistence, and also because of its ready availability to potential terrorists and its documented use in large-scale biowarfare production efforts in Iraq in the late nineteen-eighties (Arnon et al. 2001, supra; Cohen et al. *Science* 294(5542):498-501 (2001)).

The bioterrorism threat is BoNT, a "toxin weapon," rather than the rare natural infection by *C. botulinum*. BoNT is deliverable in cold foods or beverages, or as an aerosol. In a military deployment, aerosolized toxin delivered via bomb, missile, or directly sprayed from a plane would be considered the primary threat; all three delivery mechanisms were explored by the Iraq military before 1991 (Arnon et al. 2001, supra). Homeland Security concerns focus on sabotage in foodstuffs (Wein et al. 2005, supra).

Extracellular interventions are generally ineffective unless given immediately after toxin exposure. Any intervention which targets the initial steps in intoxication (binding, translocation, or endocytosis (Montal 2010, supra)) generally cannot provide benefit to neurons which are already intoxicated by intracellular LC; nor can such an intervention accelerate recovery from paralysis. Importantly, BoNT/A LC reaches its intraneuronal target site within hours after exposure and persists in neurons for months (Montal 2010, supra). Based upon the purported mechanism of action for BoNT, two efficacy profiles are possible for a small molecule intraneuronal LC inhibitor, Type I and Type II, as detailed further below. In some embodiments, a therapeutic provides both types of efficacy.

Type I Efficacy involves slowing or halting progression of intoxication. Type I efficacy results from inhibition of the intraneuronal LC activity before proteolysis of SNAP-25 has reached levels that result in functional failure of exocytosis. The window of opportunity for Type I intervention remains to be fully elucidated, but it is postulated to be significantly longer than the window for protection through systemic clearance of extracellular toxin.

Type II Efficacy involves accelerating recovery of paralyzed tissue. Type II efficacy results from inhibition of LC activity in a neuron which is already functionally incompetent in terms of exocytosis. Under this circumstance, exocytosis may be restored upon attaining functional levels of newly synthesized SNAP-25. Depending on SNAP-25 depletion at initiation of therapy and the rate of SNAP-25 turnover (Foran et al. *J. Biol. Chem.* 278(2): 1363-71 (2003)) restoration of normal function could occur in days with LC inhibitor therapy as opposed to months without it. Type II Efficacy is generally not achieved by any extraneuronal therapy.

An advanced agent may be artificially engineered to bypass existing countermeasures or produce a more severe or otherwise enhanced spectrum of disease. Genetic engineering of an infectious organism vector which could deliver BoNT LC into cells has been studied (Arnon et al. (2001), supra). Such an advanced agent, with BoNT LC delivered in a viral vector, may be unaffected by any therapeutics acting against the native toxin proteins or its entry mechanism. For defense against such a 'next generation' infectious BoNT LC advanced agent, a countermeasure directly targeting the proteolytic action of BoNT LC may be effective.

Small molecules capable of inhibiting the proteolytic activity of BoNT/A LC have been indicated (Adler et al. (2008), supra; Li et al. *Molecules* 16(1): 202-20 (2010); Dickerson et al. *Curr. Top. Med. Chem.* 14: 2094-2102 (2014)). These include small molecule inhibitors containing a hydroxamic acid zinc binding group (Pang et al. *PLoS one* 5(4): e10129 (2010); Stowe et al. *Org. Lett.* 12(4):756-9 (2010); Capek et al. *ACS Chem. Neurosci.* 2(6):288-293 (2011)). The hydroxamic acid moiety has been shown to bind to the active site zinc in several reported co-crystal structures of inhibitors bound in the active site (Silvaggi et al. *Chem. Biol.* 14:533-542 (2007)).

Other inhibitors include those based on peptides, quinolines (Burnett et al. *J. Med. Chem.* 50(9):2127-36(2007); Roxas-Duncan et al. *Antimicrob. Agents Chemother.* 53(8): 3478-3486 (2009); Caglic et al. *J. Med. Chem.* 57(3):669-676 (2014)), thiols (Moe et al. *Bioorg. Med. Chem.* 17(8): 3072-9 (2009)), polycationic small molecules (Nuss et al. *ACS Med. Chem. Lett.* 1(7): 301-5 (2010); Opsenica, Burnett et al. *J. Med. Chem.* 54(5):1157-69 (2011)), and other groups (Cai et al. *Toxicon.* 55(4): 818-826 (2010); Capkova et al. *Bioorg. Med. Chem. Lett.* 20(1):206-8 (2010); Cardinale et al. *Botulinum* J. 2(1):16-20 (2011); Silhar et al. *Bioorg. Med. Chem. Lett.* 21:2229-2231 (2011); Cardellina I I et al. *ACS Med. Chem. Lett.* 3:387-391 (2012)).

Drugs containing a hydroxamic acid zinc-binding moiety have been approved for use by the FDA. The following small molecules bearing hydroxamic acids have received FDA approval for use in humans: Verinostat (Zolinza), Belinostat (Beleodaq), Deferoxamine (Desferal), Bufexamac (Paraderm), and Panobinostat (Farydak).

In some embodiments, there are provided compounds of formula I:

I wherein $R^1$ is $-OR^5$;
m is an integer from 0 to 5;
n is an integer from 0 to 2;

each $R^2$ is independently selected from the group consisting of hydrogen, halogen, and alkyl;
$R^3$ is selected from the group consisting of hydrogen, alkyl, cycloalkyl, aryl, hydroxyalkyl, alkoxyalkyl, aryloxyalkyl, aralkyloxyalkyl, aralkyl, alkylaminoalkyl, dialkylaminoalkyl, aralkylaminoalkyl, and heterocycloalkyl;
each $R^4$ is independently hydrogen or alkyl;
$R^5$ is an alkyl; and
each of $R^2$, $R^3$, $R^4$, and $R^5$ being independently optionally substituted with hydroxy, alkoxy, halogen, or alkyl.

The one or more $R^4$ may be attached to any one or more of a C atom and/or a N atom of the pyrazolyl moiety. In some embodiments, $R^4$ is attached to a C atom of the pyrazolyl moiety. In some embodiments, $R^4$ is attached to a N atom of the pyrazolyl moiety.

In some embodiments, $R^5$ is an unsubstituted alkyl. In some embodiments, $R^5$ is an unsubstituted lower alkyl having from 1 to 6 carbons, for example, methyl, ethyl, n-propyl, isopropyl, n-butyl, isobutyl, sec-butyl, or tert-butyl, and the like.

In some embodiments, $R^5$ is a substituted alkyl group. In some embodiments, $R^5$ is substituted with one or more OH, and/or halogen (e.g., F, Cl, Br). In one embodiment, $R^5$ is substituted with OH. In one embodiment, $R^5$ is substituted with F.

In some embodiments, $R^5$ is methyl, ethyl, n-propyl, or isobutyl. In some embodiments, $R^5$ is a substituted n-propyl, for example $-OCH_2CH_2CH_2OH$, $-OCH_2CH_2CH_2F$.

In some embodiments, $R^2$ is methyl, chlorine, or fluorine. In some embodiments, one or more $R^2$ is(are) substituted at the ortho, meta, and/or para position.

In some embodiments, $R^3$ is selected from the group consisting of methyl, ethyl, isopropyl, n-propyl, cyclopropyl, n-butyl, cyclobutyl, phenyl, and benzyl.

In some embodiments, $R^3$ is isopropyl.
In some embodiments, $R^3$ is of formula $-(CH_2)_y XR_z$;
wherein y is an integer from 2 to 5;
z is 1 or 2;
X is O or N;
each R is independently selected from the group consisting of hydrogen, methyl, and optionally substituted benzyl.

In some embodiments, $R^3$ is selected from the group consisting of pyran-4-yl, 1-N-Me-piperidin-4-yl, and $-CH(CH_2OMe)_2$.

In some embodiments, the compound of Formula I is in a formate salt form. Such forms include monoformate salts, diformate salts, or triformate salts. Other salts include trifluoroacetate and chloride salts. In some embodiments, the compound of Formula I is in a salt form is selected from the group consisting of a hydrochloric acid salt, a formic acid salt, and a trifluoroacetic acid salt.

The compounds disclosed herein can exist as any therapeutically acceptable salt. The present compounds listed herein may be provided in the form of salts, such as acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. For a more complete discussion of the preparation and selection of salts, refer to Pharmaceutical Salts: Properties, Selection, and Use (Stahl, P. Heinrich. Wiley-VCHA, Zurich, Switzerland, 2002). Further exemplary salts include, without limitation, bromide, iodide, acetate, tosylate, tartrate, sulfate, succinate, phosphate, oxalate, nitrate, mesylate, maleate, malate, and citrate.

In some embodiments, $R^5$ is methyl, $R^2$ is 4-chloro, $R^3$ is isopropyl, and $R^4$ is hydrogen.

In some embodiments, $R^5$ is —OCH$_2$CH$_2$CH$_2$OH, $R^2$ is 4-chloro, $R^3$ is isopropyl, and $R^4$ is hydrogen.

In some embodiments, $R^1$ is —OR$^5$ and $R^1$ is in the R-diastereomeric configuration.

In some embodiments, $R^1$ is —OR$^5$ and $R^1$ is in the S-diastereomeric configuration.

In some embodiments, there are provided compounds of formula II:

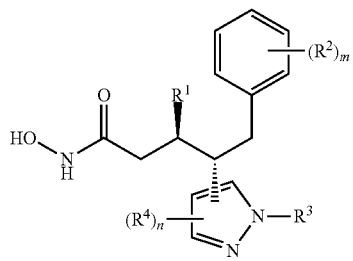

II wherein $R^1$ is —OR$^5$;
m is an integer from 0 to 5;
n is an integer from 0 to 2;
each $R^2$ is independently selected from the group consisting of hydrogen, halogen, and alkyl;
$R^3$ is selected from the group consisting of hydrogen, alkyl, cycloalkyl, aryl, hydroxyalkyl, alkoxyalkyl, aryloxyalkyl, aralkyloxyalkyl, aralkyl, alkylaminoalkyl, dialkylaminoalkyl, aralkylaminoalkyl, and heterocycloalkyl;
each $R^4$ is independently hydrogen or alkyl;
$R^5$ is an alkyl; and
each of $R^2$, $R^3$, $R^4$, and $R^5$ being independently optionally substituted with hydroxy, alkoxy, halogen, or alkyl.

The one or more $R^4$ may be attached to any one or more of a C atom and/or a N atom of the pyrazolyl moiety. In some embodiments, $R^4$ is attached to a C atom of the pyrazolyl moiety. In some embodiments, $R^4$ is attached to a N atom of the pyrazolyl moiety.

In some embodiments, $R^5$ is an unsubstituted alkyl. In some embodiments, $R^5$ is an unsubstituted lower alkyl having from 1 to 6 carbons, for example, methyl, ethyl, n-propyl, isopropyl, n-butyl, isobutyl, sec-butyl, or tert-butyl, and the like.

In some embodiments, $R^5$ is a substituted alkyl group. In some embodiments, $R^5$ is substituted with one or more OH, and/or halogen (e.g., F, Cl, Br). In one embodiment, $R^5$ is substituted with OH. In one embodiment, $R^5$ is substituted with F.

In some embodiments, $R^5$ is methyl, ethyl, n-propyl, or isobutyl. In some embodiments, $R^5$ is a substituted n-propyl, for example —OCH$_2$CH$_2$CH$_2$OH, —OCH$_2$CH$_2$CH$_2$F.

In some embodiments, $R^2$ is methyl, chlorine, or fluorine. In some embodiments, one or more $R^2$ is(are) substituted at the ortho, meta, and/or para position.

In some embodiments, $R^3$ is selected from the group consisting of methyl, ethyl, isopropyl, n-propyl, cyclopropyl, n-butyl, cyclobutyl, phenyl, and benzyl.

In some embodiments, $R^3$ is isopropyl.

In some embodiments, $R^3$ is of formula —(CH$_2$)$_y$XR$_z$;
wherein y is an integer from 2 to 5;
z is 1 or 2;
X is O or N;

each R is independently selected from the group consisting of hydrogen, methyl, and optionally substituted benzyl.

In some embodiments, $R^3$ is selected from the group consisting of pyran-4-yl, 1-N-Me-piperidin-4-yl, and —CH(CH$_2$OMe)$_2$.

In some embodiments, the compound of Formula II is in a formate salt form. Other salts include trifluoroacetate and chloride salts. In some embodiments, the compound of Formula II is in a salt form is selected from the group consisting of a hydrochloric acid salt, a formic acid salt, and a trifluoroacetic acid salt.

In some embodiments, $R^5$ is methyl, $R^2$ is 4-chloro, $R^3$ is isopropyl, and $R^4$ is hydrogen.

In some embodiments, $R^5$ is —OCH$_2$CH$_2$CH$_2$OH, $R^2$ is 4-chloro, $R^3$ is isopropyl, and $R^4$ is hydrogen.

In some embodiments, there are provided compounds of formula III:

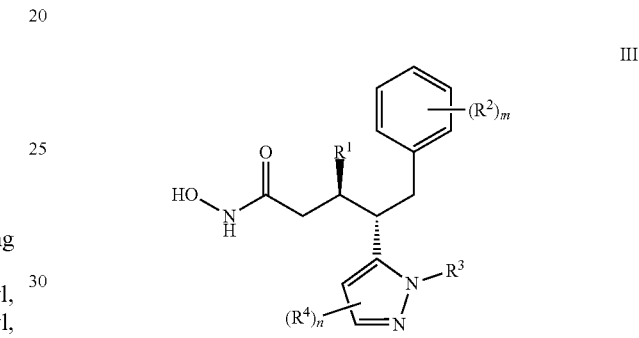

III wherein $R^1$ is —OR$^5$;
m is an integer from 0 to 5;
n is an integer from 0 to 2;
each $R^2$ is independently selected from the group consisting of hydrogen, halogen, and alkyl;
$R^3$ is selected from the group consisting of hydrogen, alkyl, cycloalkyl, aryl, hydroxyalkyl, alkoxyalkyl, aryloxyalkyl, aralkyloxyalkyl, aralkyl, alkylaminoalkyl, dialkylaminoalkyl, aralkylaminoalkyl, and heterocycloalkyl;
each $R^4$ is independently hydrogen or alkyl;
$R^5$ is an alkyl; and
each of $R^2$, $R^3$, $R^4$ and $R^5$ being independently optionally substituted with hydroxy, alkoxy, halogen, or alkyl.

The one or more $R^4$ may be attached to any one or more of a C atom and/or a N atom of the pyrazolyl moiety. In some embodiments, $R^4$ is attached to a C atom of the pyrazolyl moiety. In some embodiments, $R^4$ is attached to a N atom of the pyrazolyl moiety.

In some embodiments, $R^5$ is an unsubstituted alkyl. In some embodiments, $R^5$ is an unsubstituted lower alkyl having from 1 to 6 carbons, for example, methyl, ethyl, n-propyl, isopropyl, n-butyl, isobutyl, sec-butyl, or tert-butyl, and the like.

In some embodiments, $R^5$ is a substituted alkyl group. In some embodiments, $R^5$ is substituted with one or more OH, and/or halogen (e.g., F, Cl, Br). In one embodiment, $R^5$ is substituted with OH. In one embodiment, $R^5$ is substituted with F.

In some embodiments, $R^5$ is methyl, ethyl, n-propyl, or isobutyl. In some embodiments, $R^5$ is a substituted n-propyl, for example —OCH$_2$CH$_2$CH$_2$OH, —OCH$_2$CH$_2$CH$_2$F.

In some embodiments, $R^2$ is methyl, chlorine, or fluorine. In some embodiments, one or more $R^2$ is(are) substituted at the ortho, meta, and/or para position.

In some embodiments, $R^3$ is selected from the group consisting of methyl, ethyl, isopropyl, n-propyl, cyclopropyl, n-butyl, cyclobutyl, phenyl, and benzyl.

In some embodiments, $R^3$ is isopropyl.

In some embodiments, $R^3$ is of formula —$(CH_2)_y XR_z$; wherein y is an integer from 2 to 5;

z is 1 or 2;

X is O or N;

each R is independently selected from the group consisting of hydrogen, methyl, and optionally substituted benzyl.

In some embodiments, $R^3$ is selected from the group consisting of pyran-4-yl, 1-N-Me-piperidin-4-yl, and —CH$(CH_2OMe)_2$.

In some embodiments, the compound of Formula III is in a formate salt form. Other salts include trifluoroacetate and chloride salts. In some embodiments, the compound of Formula III is in a salt form is selected from the group consisting of a hydrochloric acid salt, a formic acid salt, and a trifluoroacetic acid salt.

In some embodiments, $R^5$ is methyl, $R^2$ is 4-chloro, $R^3$ is isopropyl, and $R^4$ is hydrogen.

In some embodiments, $R^5$ is —$OCH_2CH_2CH_2OH$, $R^2$ is 4-chloro, $R^3$ is isopropyl, and $R^4$ is hydrogen.

In some embodiments, there are provided compounds selected from any one of Examples in Tables 1-5, hereinbelow.

In some embodiments, there are provided compounds of formula IV:

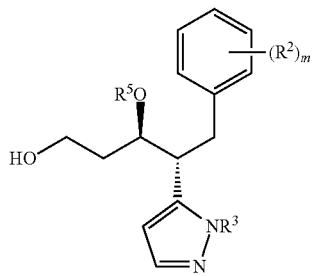

IV each $R^2$ is independently selected from the group consisting of hydrogen, halogen, and alkyl;

$R^3$ is selected from the group consisting of hydrogen, alkyl, cycloalkyl, aryl, hydroxyalkyl, alkoxyalkyl, aryloxyalkyl, aralkyloxyalkyl, aralkyl, alkylaminoalkyl, dialkylaminoalkyl, aralkylaminoalkyl, and heterocycloalkyl;

$R^5$ is methyl or ethyl;

each of $R^2$, $R^3$, and $R^5$ being independently optionally substituted with hydroxy, alkoxy, halogen, or alkyl, and m is an integer from 0 to 5.

In some embodiments, $R^5$ is methyl, $R^2$ is 4-chloro, and $R^3$ is isopropyl.

In some embodiments, the compound of Formula IV is in a salt form is selected from the group consisting of a hydrochloric acid salt, a formic acid salt, and a trifluoroacetic acid salt.

Pharmaceutical Composition

In some embodiments, there are provided pharmaceutical compositions comprising a compound according one or more of the previous embodiments along with a pharmaceutically acceptable carrier. Thus, while it may be possible for the compounds disclosed herein to be administered as the raw chemical, it is also possible to present them as a pharmaceutical formulation. Accordingly, there are provided pharmaceutical formulations comprising a compound or a pharmaceutically acceptable salt, ester, prodrug or solvate thereof, together with one or more pharmaceutically acceptable carriers thereof and optionally one or more other therapeutic ingredients. The carrier(s) are "acceptable" in the sense of being compatible with the other ingredients of the formulation and not deleterious to the recipient thereof. Proper formulation is dependent upon the route of administration chosen.

Typical pharmaceutical compositions include a compound as disclosed herein in a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example, contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents or flavoring agents. The compositions can also be sterilized if desired.

Any of the well-known techniques, carriers, and excipients may be used as suitable and as understood in the art; e.g., in Remington's Pharmaceutical Sciences. The pharmaceutical compositions may be manufactured in a manner that is itself known, e.g., by means of conventional mixing, dissolving, granulating, dragee-making, levigating, emulsifying, encapsulating, entrapping or compression processes.

Modes of Administration

The compounds of the disclosure may be administered to the subject in a therapeutically effective amount orally, intravenously, subcutaneously, intramuscularly or any other method known to those skilled in the art (e.g., rectal, parenteral). For oral administration, the compositions may be in the form of compressed tablets, dragees or capsules prepared by conventional means using known supports and excipients such as binders, fillers, lubricants or disintegration agents; alternatively they may be in the form of solutions, syrups or suspensions.

For administration in the form of injectable solutes, the compound may be prepared as a solution or suspension capable of being administered by injection. A suitable pharmaceutical composition may be made for sterile injection containing between 1 and 50% w/w of the compounds used in the disclosure.

In certain cases, it may be useful to formulate the compounds of the disclosure in suppository form or as extended release formulation for deposit under the skin or intramuscular injection. For each type of administration appropriate pharmaceutical excipients are likely to be added to the drug. The nature of such excipients for each type of systemic administration is well known in the art and need not be described here further.

A useful therapeutic or prophylactic concentration will vary from with the precise identity of the drug, with the severity of the *botulinum* toxin infection being treated and the subject's susceptibility to treatment. Accordingly, no single concentration will be uniformly useful, but will require modification depending on the particularities of each situation. However, it is anticipated that an amount between 1.0 and 10 mg per kg of body weight per day will affect a therapeutic result.

Method of Treatments

In some embodiments, there are provided methods of treating a subject exposed to a *botulinum* toxin comprising administering to the subject a pharmaceutical composition comprising a compound according to one or more of the previous embodiments.

In some embodiments, the compounds of formulas I-IV or pharmaceutical acceptable salts, enantiomers, diastereomers or prodrug or mixture thereof may be useful for the treating a subject exposed to a *botulinum* toxin. The compounds of formula I-IV may be used alone, or in combination with one or more active agent to effectively treat *botulinum* toxin infection. Examples of active agents include, but are not limited to, heptavalent *botulinum* antitoxin (HBAT).

In embodiments, the disclosure provides the use of a compound of formulas I-IV for the production of a medicament for the treatment or prophylaxis of *botulinum* toxin infection. In embodiments, the disclosure provides the use of a compound of formula I-IV for the production of a medicament for inhibiting BoNT/A LC.

In embodiments, a method is provided for the preparation of a medicament useful for the treatment or *botulinum* toxin infection, where the medicament comprising a pharmaceutical composition disclosed herein.

In embodiments, there are provided methods of treating a subject exposed to a *botulinum* toxin by administering to the subject a pharmaceutical composition comprising a compound according to one or more of the previous embodiments. In these embodiments, a method is provided for inhibiting the activity of BoNT/A LC.

Definitions

The term "acyl," as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene [—CH=CH—]. Examples of suitable alkenyl groups include ethenyl, propenyl, 2-methylpropenyl, 1,4-butadienyl and the like. Unless otherwise specified, the term "alkenyl" may include "alkenylene" groups.

In some embodiments, the term "alkoxy" refers to an alkyl ether group, wherein the term alkyl is as defined below. Examples of alkyl ether groups include methoxy, ethoxy, n-propoxy, isopropoxy, n-butoxy, iso-butoxy, sec-butoxy, tert-butoxy, and the like. Alternatively, the term "alkoxy" refers to the group —OR$_5$, wherein R$_5$ can be a substituted or an unsubstituted alkyl.

The term "alkoxyalkyl," as used herein, alone or in combination, refers to an alkoxy group attached to the parent molecular moiety through an alkyl group. The term "alkoxyalkyl" also embraces alkoxyalkyl groups having one or more alkoxy groups attached to the alkyl group, that is, to form monoalkoxyalkyl and dialkoxyalkyl groups.

The term "alkyl," as used herein, alone or in combination, refers to a straight-chain or branched-chain alkyl group containing from 1 to 20 carbon atoms. In certain embodiments, the alkyl group will comprise from 1 to 10 carbon atoms. In further embodiments, the alkyl group will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The terms "alkylamino" and "dialkylamino" as used herein, alone or in combination, refers to an alkyl group, as defined herein, having an amino group attached thereto. Suitable alkylamino and dialkylamino groups may be mono- or dialkylated, respectively, forming groups such as, for example, N-methylamino, N-ethylamino, N,N-dimethylamino, N,N-diethylamino and the like.

The term "alkylaminoalkyl" as used herein, alone or in combination, refers to an alkylamino group attached to the parent molecular moiety through an alkyl group.

The terms "amido" is interchangeable with "carbamoyl," and as used herein, alone or in combination, refer to an amino group as described below attached to the parent molecular moiety through a carbonyl group, or vice versa. The term "C-amido" as used herein, alone or in combination, refers to a —C(O)—NR$_2$ group with R as defined herein. The term "N-amido" as used herein, alone or in combination, refers to a RC(O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aralkyl" or "arylalkyl," as used herein, alone or in combination, refers to an aryl group attached to the parent molecular moiety through an alkyl group. The aralkyl may be optionally substituted.

The term "aryl," as used herein, alone or in combination, refers to a carbocyclic aromatic system containing one, two or three rings wherein such rings may be attached together in a pendent manner or may be fused. The term "aryl" embraces aromatic radicals such as benzyl, phenyl, naphthyl, and biphenyl. The aryl may be optionally substituted.

The term "aryloxy," as used herein, alone or in combination, refers to an aryl group having an oxygen atom attached thereto.

The term "aryloxyalkyl," as used herein, alone or in combination, refers to a radical of the formula aryl-O-alkyl, in which the terms "aryl" and "alkyl" are defined herein. In some embodiments, the term "aryloxyalkyl" refers to an aryl attached to an oxygen atom which in turn attached to the parent molecular moiety through an alkyl group.

The term "aralkyloxy," as used herein, alone or in combination, refers to a lower alkoxy having 1 to 6 carbon atoms substituted with an aryl group. The aralkyloxy may be optionally substituted. Examples of aralkyloxy includes, for example, benzyloxy, methylbenzyloxy, phenethyloxy and the like.

The term "aralkyloxyalkyl," as used herein, alone or in combination, refers to an aralkyloxy attached to the parent molecular moiety through an alkyl group. The aralkyloxyalkyl may be optionally substituted.

The term "aralkylamino" as used herein, alone or in combination, refers to an amino group which is substituted with one or two aralkyl radicals, as defined herein.

The term "aralkylaminoalkyl" as used herein, alone or in combination, refers to an aralkylaminoalkyl group attached to the parent molecular moiety through an alkyl group. The aralkylaminoalkyl may be optionally substituted.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cycloalkyl," as used herein, alone or in combination, refers to an aliphatic cyclic alkyl moiety wherein the ring is either completely saturated, partially unsaturated, or fully unsaturated, wherein if there is unsaturation, the conjugation of the pi-electrons in the ring do not give rise to aromaticity. A cycloalkyl group may be optionally substituted. Preferred cycloalkyl groups include groups having from 3 to 10 ring atoms, or from 3 to 6 ring atoms. The term "carbocyclic cycloalkyl" refers to a monocyclic or polycyclic cycloalkyl group which contains only carbon and hydrogen. The term "heterocycloalkyl" refers to a monocyclic or polycyclic cycloalkyl group wherein at least one ring backbone contains at least one atom which is different from carbon.

The term "halo," or "halogen," as used herein, alone or in combination, refers to fluorine, chlorine, bromine, or iodine.

The term "heterocyclyl," as used herein, alone or in combination as in "heterocyclylmethyl", refers to a stable cyclic hydrocarbon group, fully saturated or containing from 1 to 3 degrees of unsaturation, consisting of from one to three heteroatoms chosen from O, N, and S, and wherein the nitrogen and sulfur atoms may optionally be oxidized and the nitrogen heteroatom may optionally be quaternized. The heterocycle groups may be optionally substituted unless specifically prohibited.

The term "hydroxyalkyl," as used herein, alone or in combination, refers to a hydroxy group attached to the parent molecular moiety through an alkyl group.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

The term "optionally substituted" means the group may be substituted or unsubstituted. When substituted, the substituents of an "optionally substituted" group may include, without limitation, one or more substituents independently selected from the following groups or a particular designated set of groups, alone or in combination: acyl, lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art.

The term "inhibition" (and by extension, "inhibitor") as used herein encompasses all forms of functional protein (enzyme, kinase, receptor, channel, etc., for example) inhibition, including neutral antagonism, inverse agonism, competitive inhibition, and non-competitive inhibition (such as allosteric inhibition). Inhibition may be stated in terms of an IC50 or Ki value.

As used herein, reference to "treatment" or "treating" of a subject is intended to include pre- or post-exposure prophylaxis.

As used herein, the term "medicament" refers to any substance or combination of substances that has a beneficial and/or therapeutic effect.

As used herein, the term "subject" (as in the subject of the treatment) means both mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The term "compound," as used herein, includes salts, solvates and polymorphs of the compound, as well as the free base. In certain embodiments, the solvate is a hydrate. A solvate is a stable, solid or semi-solid form of a compound that comprises either a non-stoichiometric or a stoichiometric equivalent of solvent. If the solvent is water, the solvate is a hydrate. In certain embodiments, the hydrate has a stoichiometric equivalent of water chosen from about 0, about 0.5, and about $1H_2O$; that is, the hydrate is anhydrous, a hemihydrate, or a monohydrate. Non-stoichiometric hydrates and stoichiometric hydrates are both contemplated. As further discussed below, a polymorph is a distinct crystalline form of a compound. A compound may be, for example, a polymorph of a free base, a polymorph of a salt, a polymorph of a hydrate, or a polymorph of a hydrate of a salt of a compound, and so forth.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

EXAMPLES

This example describes an exemplary BoNT/A LC assay.

In a 96 well, clear bottom black plate, the following was added to each well: 5 nM BoNT/A $LC_{1-429}$, 28 μM substrate in 30 mM HEPES pH 7.3, 0.05 mM zinc acetate, 0.05% Tween 20 for a total volume of 100 μL. Varying concentrations of inhibitor were added with a final DMSO concentration of 2.5%. The rate of enzymatic activity (RFU/sec) was monitored by a 60 minute kinetic read at ex 320 nm, em 420 nm.

Substrate: Abz-Thr-dArg-Ile-Asp-Glu-Ala-Asn-Gln-Arg-Ala-Thr-Lys-Nle-Lys(Dnp)-$NH_2$ (SEQ ID NO:1); $\lambda_{ex}$=320 nm, $\lambda_{em}$=420 nm HBI BoNT/A $LC_{1-429}$ construct (Hall A1):

BoNT/A $LC_{429}$ Enzymatic assay construct:

(SEQ ID NO: 2)

```
MRHHHHHHGAQMPFVNKQFNYKDPVNGVDIAYIKIPNAGQMQPVKAFKIHN

KIWVIPERDTFTNPEEGDLNPPPEAKQVPVSYYDSTYLSTDNEKDNYLKGV
```

-continued

```
TKLFERIYSTDLGRMLLTSIVRGIPFWGGSTIDTELKVIDTNCINVIQPDG

SYRSEELNLVIIGPSADIIQFECKSFGHEVLNLTRNGYGSTQYIRFSPDFT

FGFEESLEVDTNPLLGAGKFATDPAVTLAHELIHAGHRLYGIAINPNRVFK

VNTNAYYEMSGLEVSFEELRTFGGHDAKFIDSLQENEFRLYYYNKFKDIAS

TLNKAKSIVGTTASLQYMKNVFKEKYLLSEDTSGKFSVDKLKFDKLYKMLT

EIYTEDNFVKFFKVLNRKTYLNFDKAVFKINIVPKVNYTIYDGFNLRNTNL

AANFNGQNTEINNMNFTKLKNFTGLFEFYKLL
```

Tables 1 through 5 below show the results of application of this assay to small molecule hydroxamic acid compounds in accordance with embodiments herein.

TABLE 1

| Example No. | $R^5$ | $R^2$ | $R^3$ | $K_i$ (nM) |
|---|---|---|---|---|
| 1-1 | Me | 4-Cl | —iPr | 6.1 |
| 1-2 | Me | 4-Cl | —$CH_3$ | 21.3 |
| 1-3 (HCl) | Me | 4-Cl | —$CH_3$ | 6.4 |
| 1-4 | Me | 4-Cl | —$CH_2CH_3$ | 13.8 |
| 1-5 | Me | 4-Cl | —$(CH_2)_2$—$CH_3$ | 3.2 |
| 1-6 | Me | 4-Cl | —$(CH_2)_2$—OH | 18.0 |
| 1-7 | Me | 4-Cl | —$(CH_2)_3$—$CH_3$ | 6.2 |
| 1-8 | Me | 4-Cl | —$(CH_2)_2$—OMe | 14.7 |
| 1-9 | Me | 4-Cl | —$(CH_2)_3$—OH | 8.2 |
| 1-10 | Me | 4-Cl | —$(CH_2)_2$—$OCH_2Ph$ | 39.8 |
| 1-11 | Me | 4-Cl | —$(CH_2)_3$—$OCH_2Ph$ | 44.0 |
| 1-12 | Me | 4-Cl | —$(CH_2)_5$—$N(Me)_2$ | 28.0 |
| 1-13 (formate) | Me | 4-Cl | —$(CH_2)_4$—NHMe | 19.0 |
| 1-14 (formate) | Me | 4-Cl | —$(CH_2)_4$—$NHCH_2$—(4-F—Ph) | 20.4 |
| 1-15 (TFA) | Me | 4-Cl | —$CH_2Ph$ | 17.8 |

TABLE 2

| Example No. | $R^5$ | $R^2$ | $R^3$ | $K_i$ (nM) |
|---|---|---|---|---|
| 1-1 | Me | 4-Cl | —iPr | 6.1 |
| 2-1 (HCl) | Me | 4-Cl | —iPr | 5.7 |
| 2-2 | Et | 4-Cl | —iPr | 24.5 |
| 2-3 | Me | 4-F | —iPr | 26.0 |
| 2-4 | Me | 2-Me, 4-F | —iPr | 4.5 |
| 2-5 | Me | 3-Me, 4-F | —iPr | 214.5 |
| 2-6 | Me | 4-Me | —iPr | 117.5 |

TABLE 3

| Example No. | R⁵ | R² | R³ | $K_i$ (nM) |
|---|---|---|---|---|
| 1-1 | Me | 4-Cl | —iPr | 6.1 |
| 3-1 | Me | 2-Me, 4-F | —CH₃ | 10.2 |
| 3-2 | Me | 2-Me, 4-F | -cyclopropyl | 5.4 |
| 3-3 | Me | 3-Me, 4-F | -cyclopropyl | 623.0 |
| 3-4 | Me | 4-Me | -cyclopropyl | 207.0 |
| 3-5 | Me | 4-Cl | -cyclopropyl | 6.4 |
| 3-6 | Me | 4-Cl | -cyclobutyl | 9.5 |
| 3-7 | Me | 4-Cl | -pyran-4-yl | 5.1 |
| 3-8 | Me | 4-Cl | -1-N-Me-piperidin-4-yl | 5.4 |
| 3-9 | Me | 4-Cl | —CH(CH₂OMe)₂ | 31.7 |
| 3-10 | Me | 4-Cl | —Ph | 30.6 |
| 3-11 (HCl) | Me | 4-Cl | —Ph | 53.0 |

TABLE 4

| Example No. | R⁵ | R² | R³ | R⁴ | $K_i$ (nM) |
|---|---|---|---|---|---|
| 4-1 | Me | 4-Cl | Me | Me | 182.0 |
| 4-2 | Me | 4-Cl | iso-propyl | H | 33.3 |

Table A below summarizes the abbreviations used in conjunction with the synthetic Schemes below.

TABLE A

| | |
|---|---|
| Bu₂BOTf | dibutylboron trifluoromethanesulfonate |
| CD₃OD | tetradeuterated methanol, methanol-d4 |
| cm | centimeters |
| DCM | dichloromethane |
| DIEA | N,N-diisopropylethylamine |
| Et₃N | triethylamine |
| EtOH | ethanol |
| GC/MS | tandem gas chromatography/mass spectrometry |
| Hz | hertz |
| IR | infared spectroscopy |
| J | Coupling constant |
| Jones oxidation reagent, Jones reagent | H₂CrO₄/H₂SO₄/H₂O |
| KCN | potassium cyanide |
| LC/MS | tandem liquid chromatography/mass spectrometry |
| LiCl | lithium chloride |

TABLE A-continued

| | |
|---|---|
| M | molar |
| M⁺ | molecular ion |
| (M + H)⁺ | protonated molecular ion |
| MeI | methyl iodide or iodomethane |
| MeOH | methanol |
| Me₃Al | trimethylaluminum |
| MHz | megahertz |
| min | minutes |
| mL | milliliter |
| mmol | millimole |
| MS(API-ES) | mass spectrometry (atmospheric pressure ionization-electrospray) |
| MS (EI) | mass spectrometry(electron impact) |
| N | normal |
| N₂ | nitrogen (gas) |
| NaH | sodium hydride |
| Na₂SO₄ | sodium sulfate |
| NH₄Cl | ammonium chloride |
| NH₂OH | hydroxylamine |
| NMR | nuclear magnetic resonance spectroscopy |
| THF | tetrahydrofuran |
| TMSCHN₂ | trimethylsilyldiazomethane |
| $t_R$ | retention time |
| δ | chemical shift in parts per million (NMR) |

Synthesis of Exemplary Compounds-Scheme I

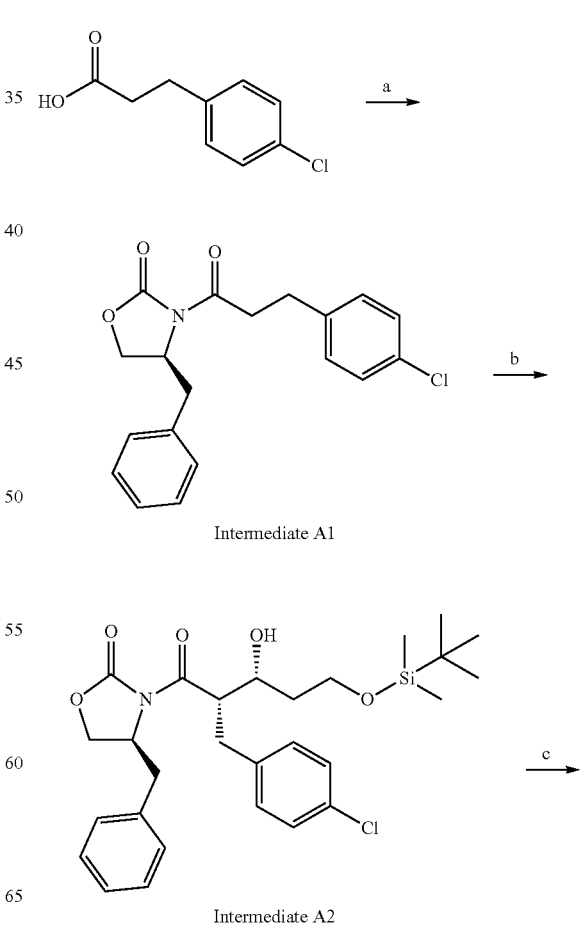

Intermediate A1

Intermediate A2

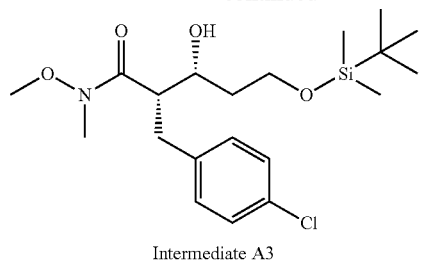

Intermediate A3

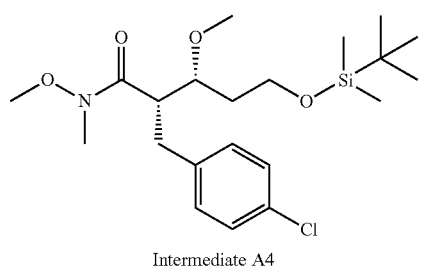

Intermediate A4

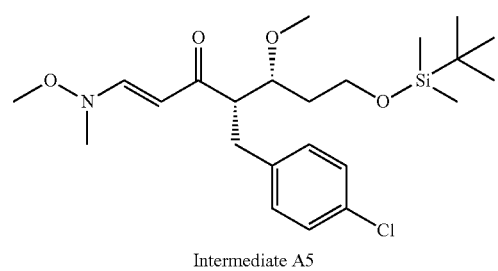

Intermediate A5

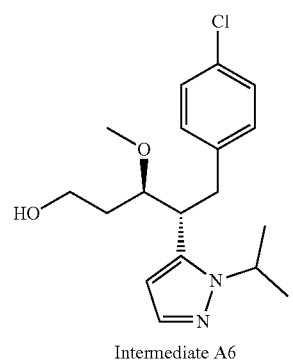

Intermediate A6

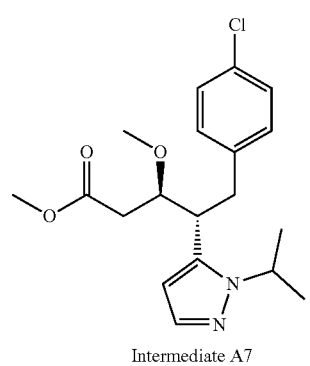

Intermediate A7

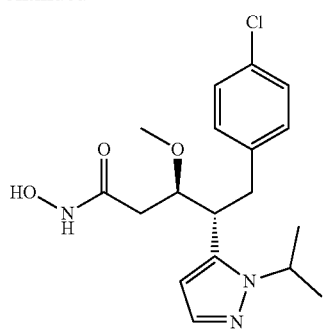

Compound 1-1

Reagents and conditions: (a) (S)-4-benzyloxazolidin-2-one, trimethylacetyl chloride, Et$_3$N, LiCl, THF, -10° C. to 25° C.; (b) 3-((tert-butyldimethylsilyl)oxy)propanal, Bu$_2$BOTf, DIEA, DCM, 0° C. to -78° C. to 25° C. to 0° C.; (c) N,O-dimethylhydroxylamine hydrochloride, Me$_3$Al, DCM, 0° C. to 25° C. to 0° C.; (d) MeI, NaH, THF, 0° C.; (e) ethynylmagnesium bromide, THF, 25° C.; (f) isopropyl hydrazine dihydrochloride, EtOH, 80° C., (g) Jones reagent, acetone, 0° C. to 25° C.; (h) TMSCHN$_2$, MeOH, DCM, 25° C.; (i) 50% NH$_2$OH—H$_2$O, KCN, THF, i-PrOH, 25° C.

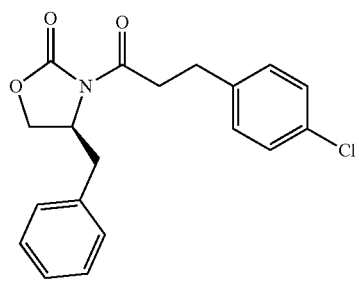 [SMILES: O=C(CCc1ccc(Cl)cc1)N1C(=O)OC[C@@H]1Cc1ccccc1]

(S)-4-Benzyl-3-(3-(4-chlorophenyl)propanoyl)oxazolidin-2-one (Intermediate A1)

To a solution of 3-(4-chlorophenyl)propanoic acid (5.000 g, 27.08 mmol) in 100 mL THF pre-cooled to -10° C., triethylamine (10.2 mL, 73.1 mmol) was added, followed by pivaloyl chloride (3.7 mL, 30 mmol). The reaction mixture was stirred at -10° C. under N$_2$ for 1 hour. Then lithium chloride (1.263 g, 29.79 mmol) was added, followed by (S)-4-benzyloxazolidin-2-one (5.279 g, 29.79 mmol). After stirring at -10° C. under N$_2$ for 1 hour, the reaction mixture was allowed to warm to room temperature overnight. The reaction mixture was then diluted with water (100 mL) and extracted with ethyl acetate (3×80 mL). The combined organic extracts were dried over anhydrous Na$_2$SO$_4$, filtered, and concentrated under reduced pressure. The resulting residue was purified by silica gel chromatography with 0-100% DCM/hexanes to give the desired product as a white solid (6.637 g). GC/MS (Method C): purity 100%; $t_R$=6.4 min; M$^+$=343.

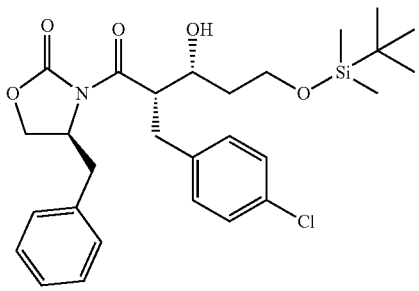 [SMILES: CC(C)(C)[Si](C)(C)OCC[C@@H](O)[C@H](Cc1ccc(Cl)cc1)C(=O)N1C(=O)OC[C@@H]1Cc1ccccc1]

(S)-4-benzyl-3-((2S,3R)-5-((tert-butyldimethylsilyl)oxy)-2-(4-chlorobenzyl)-3-hydroxypentanoyl)oxazolidin-2-one (Intermediate A2)

To a solution of (S)-4-benzyl-3-(3-(4-chlorophenyl)propanoyl)oxazolidin-2-one (7.856 g, 22.85 mmol) in 120 mL of THF pre-cooled to 0° C., Bu$_2$BOTf (10.35 mL, 47.99 mmol) was added, followed by DIEA (9.55 mL, 54.8 mmol). After stirring at 0° C. under N$_2$ for 1 hour, the reaction mixture was cooled to −78° C. Then 3-((tert-butyldimethylsilyl)oxy)propanal (6.3 mL, 30 mmol) was added. After stirring at −78° C. for 1 hour, the reaction mixture was warmed to 25° C. for 3 hour and then cooled to 0° C. A mixture of pH 7 phosphate buffer/methanol (2:5, 140 mL) was added, followed by a mixture of methanol/30% H$_2$O$_2$ (2:1, 120 mL). After stirring at 0° C. for 1 hour, the reaction mixture was separated. The aqueous layer was extracted with DCM (3×80 mL). The combined organic extracts were dried over anhydrous Na$_2$SO$_4$, filtered, and concentrated under reduced pressure. The resulting residue was purified by silica gel chromatography eluting with 0-30% ethyl acetate/hexanes to give the desired product as a colorless oil (11.925 g). LC/MS (Method A): purity>90%; $t_R$=11.0 min; (M+H)$^+$=532.

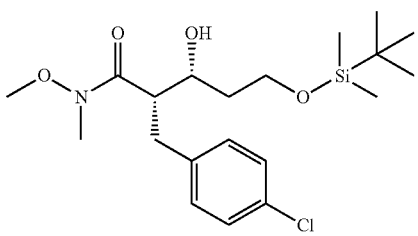 [SMILES: CON(C)C(=O)[C@@H](Cc1ccc(Cl)cc1)[C@H](O)CCO[Si](C)(C)C(C)(C)C]

(2S,3R)-5-((tert-butyldimethylsilyl)oxy)-2-(4-chlorobenzyl)-3-hydroxy-N-methoxy-N-methylpentanamide (Intermediate A3)

To a suspension of N,O-dimethylhydroxylamine hydrochloride (3.845 g, 39.42 mmol) in 50 mL DCM pre-cooled to 0° C., was added a solution of Me$_3$Al in toluene (2.0 M, 19.7 mL, 39.4 mmol). After warming to 25° C. and stirring at this temperature for 1 hour under N$_2$, the reaction mixture was cooled to 0° C. A solution of (S)-4-benzyl-3-((2S,3R)-5-((tert-butyldimethylsilyl)oxy)-2-(4-chlorobenzyl)-3-hydroxypentanoyl)oxazolidin-2-one (6.992 g, 13.14 mmol) in 15 mL of DCM was added. The reaction mixture was stirred at 0° C. for 6 hours, and then poured into a mixture of DCM/1N HCl (1:1, 200 mL). After separation, the aqueous layer was extracted with DCM (3×80 mL). The combined organic extracts were dried over anhydrous Na$_2$SO$_4$, filtered, and concentrated under reduced pressure. The resulting residue was purified by silica gel chromatography eluting with 0-40% ethyl acetate/hexanes to give the desired product as a colorless oil (4.629 g). GC/MS (Method C): purity 100%; $t_R$=5.3 min; M$^+$=415.

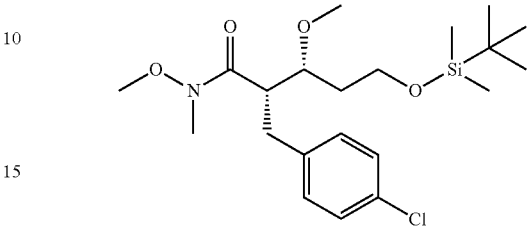

(2S,3R)-5-((tert-butyldimethylsilyl)oxy)-2-(4-chlorobenzyl)-N,3-dimethoxy-N-methylpentanamide (Intermediate A4)

To a solution of (2S,3R)-5-((tert-butyldimethylsilyl)oxy)-2-(4-chlorobenzyl)-3-hydroxy-N-methoxy-N-methylpentanamide (2.224 g, 5.346 mmol) in 30 mL of THF pre-cooled to 0° C., NaH (60% in mineral oil, 1.069 g, 26.73 mmol) was added. After the reaction mixture was stirred at 0° C. for 15 minutes, MeI (6.7 mL, 106 mmol) was added. After stirring at 0° C. under N$_2$ for 3 hours, the reaction mixture was quenched with water and extracted with DCM (3×60 mL). The combined organic extracts were dried over anhydrous Na$_2$SO$_4$, filtered, and concentrated under reduced pressure. The resulting residue was purified by silica gel chromatography eluting with 0-40% ethyl acetate/hexanes to give the desired product as a colorless oil (1.814 g). GC/MS (Method C): purity 100%; $t_R$=5.1 min; M$^+$=430.

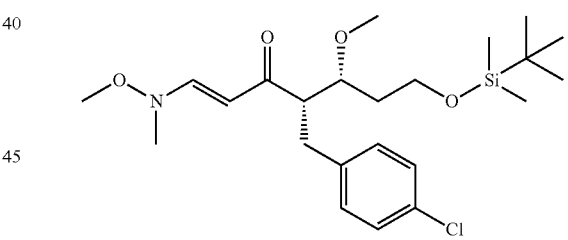

(7S,8R,E)-7-(4-chlorobenzyl)-8-methoxy-3,12,12,13,13-pentamethyl-2,11-dioxa-3-aza-12-silatetradec-4-en-6-one (Intermediate A5)

To a solution of (2S,3R)-5-((tert-butyldimethylsilyl)oxy)-2-(4-chlorobenzyl)-N,3-dimethoxy-N-methylpentanamide (1.814 g, 4.219 mmol) in 50 mL of THF, ethynylmagnesium bromide (0.5 M in THF, 84 mL, 42 mmol) was added. The reaction mixture was stirred at 25° C. for 3 hours. Then saturated NH$_4$Cl solution (100 mL) and ethyl acetate (100 mL) were added, followed by N,O-dimethylhydroxylamine hydrochloride (0.206 g, 2.11 mmol). After stirring at room temperature for 1 hour, the reaction mixture was separated. The aqueous layer was extracted with ethyl acetate (3×60 mL). The combined organic extracts were dried over anhydrous Na$_2$SO$_4$, filtered, and concentrated under reduced pressure. The resulting residue was purified by silica gel chromatography eluting with 0-45% ethyl acetate/hexanes to give the desired product as a brown oil (1.916 g). GC/MS (Method C): purity 100%; $t_R$=6.0 min; M+=455.

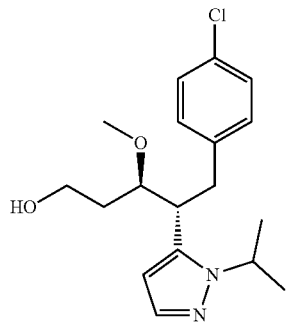 [SMILES: CO[C@H](CCO)[C@H](Cc1ccc(Cl)cc1)c1ccnn1C(C)C]

(3R,4R)-5-(4-chlorophenyl)-4-(1-isopropyl-1H-pyrazol-5-yl)-3-methoxypentan-1-ol (Intermediate A6)

(7S,8R,E)-7-(4-chlorobenzyl)-8-methoxy-3,12,12,13,13-pentamethyl-2,11-dioxa-3-aza-12-silatetradec-4-en-6-one (3.823 g, 8.850 mmol) and isopropyl hydrazine dihydrochloride (1.562 g, 10.62 mmol) were weighed into a round-bottomed flask. EtOH (60 mL) was added. The reaction mixture was heated to 80° C. overnight. After cooling to room temperature, the reaction mixture was concentrated under reduced pressure. The resulting residue was purified by silica gel chromatography eluting with 0-15% EtOH/DCM to give the desired product as a yellow solid (2.057 g). GC/MS (Method C): purity 100%; $t_R$=4.6 min; M+=336.

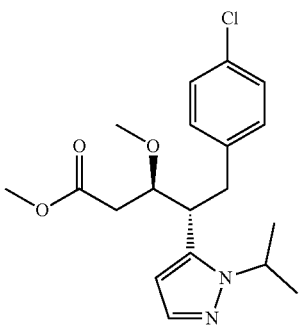 [SMILES: COC(=O)C[C@@H](OC)[C@H](Cc1ccc(Cl)cc1)c1ccnn1C(C)C]

Methyl (3R,4R)-5-(4-chlorophenyl)-4-(1-isopropyl-1H-pyrazol-5-yl)-3-methoxypentanoate (Intermediate A7)

To a solution of (3R,4R)-5-(4-chlorophenyl)-4-(1-isopropyl-M-pyrazol-5-yl)-3-methoxypentan-1-ol (1.036 g, 3.074 mmol) in 30 mL of acetone pre-cooled to 0° C. was added Jones reagent (2.0 M, 4.6 mL, 9.2 mmol). After stirring at 0° C. for 5 minutes, and then at 25° C. for 10 minutes, the reaction mixture was quenched with water (100 mL) and extracted with ethyl acetate (3×80 mL). The combined organic extracts were dried over anhydrous $Na_2SO_4$, filtered, and concentrated under reduced pressure. The resulting residue was used directly in the next step without further purification.

The crude residue was dissolved in 60 mL of MeOH/DCM (1:5). TMSCHN2 (2.0 M in Hexanes, 4.6 mL, 9.2 mmol) was added. After stirring at 25° C. for 1 hour, the reaction mixture was concentrated under reduced pressure. The resulting residue was purified by silica gel chromatography eluting with 0-70% ethyl acetate/hexanes to give the desired product as a yellow gum (0.741 g). GC/MS (Method C): purity 94%; $t_R$=4.4 min; M+=364.

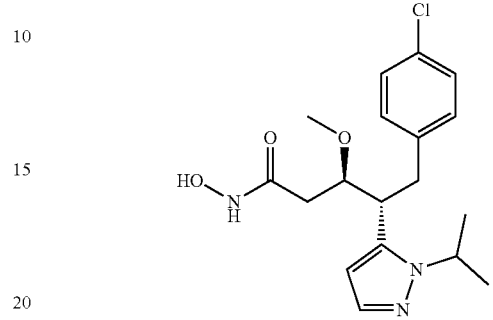

(3R,4R)-5-(4-chlorophenyl)-N-hydroxy-4-(1-isopropyl-1H-pyrazol-5-yl)-3-methoxypentanamide (Compound 1-1)

To a solution of methyl (3R,4R)-5-(4-chlorophenyl)-4-(1-isopropyl-M-pyrazol-5-yl)-3-methoxypentanoate (0.741 g, 2.03 mmol) in 16 mL of i-PrOH/THF (1:1) was added a solution of $NH_2OH$ in $H_2O$ (50%, 4 mL), followed by KCN (0.007 g, 0.1 mmol). After stirring at room temperature overnight, the reaction mixture was concentrated under reduced pressure. The resulting residue was purified by amine-functionalized silica gel chromatography eluting with 0-15% EtOH/DCM to give the desired product as a white solid (0.608 g). LC/MS (Method A): purity>98%; $t_R$=4.3 min; (M+H)+=366. $^1$H NMR (500 MHz, $CD_3OD$) δ 7.43 (d, J=1.5 Hz, 1H), 7.15 (d, J=7.5 Hz, 2H), 7.01 (d, J=7.5 Hz, 2H), 6.27 (d, J=1.5 Hz, 1H), 4.30-4.24 (m, 1H), 3.86-3.83 (m, 1H), 3.62-3.56 (m, 1H), 3.41 (s, 3H), 3.24 (dd, J=15, 5 Hz, 1H), 2.77 (dd, J=15, 5 Hz, 1H), 2.25 (dd, J=15, 5 Hz, 1H), 2.11 (dd, J=15, 5 Hz, 1H), 1.30 (d, J=10 Hz, 3H), 0.82 (d, J=10 Hz, 3H); $^{13}$C NMR (125.7 MHz, $CD_3OD$) δ 170.33, 145.29, 143.30, 139.34, 133.09, 131.80, 129.29, 104.99, 82.24, 59.23, 50.37, 44.15, 38.37, 36.57, 22.97, 22.56.

Characterizing Data for Exemplary Compounds

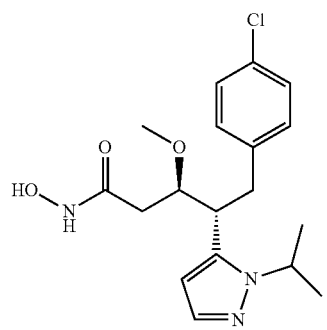 [SMILES: CO[C@H](CC(=O)NO)[C@H](Cc1ccc(Cl)cc1)c1ccnn1C(C)C]

(3R,4R)-5-(4-chlorophenyl)-N-hydroxy-4-(1-isopropyl-1H-pyrazol-5-yl)-3-methoxypentanamide (Compound 1-1): LC/MS (Method A): $t_R$=4.3 min, (M+H)+=366 (ES-API); IR: v=3217.37, 2939.61, 1681.98, 1423.51, 1203.62, 800.49, 721.40 $cm^{-1}$.

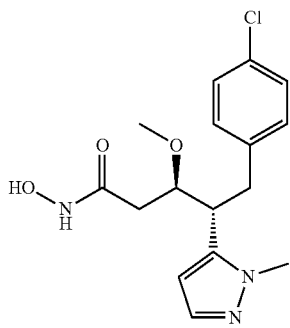 [SMILES: CO[C@H](CC(=O)NO)[C@H](Cc1ccc(Cl)cc1)c1ccnn1C]

(3R,4R)-5-(4-chlorophenyl)-N-hydroxy-3-methoxy-4-(1-methyl-M-pyrazol-3-yl)pentanamide (Compound 1-2): LC/MS (Method A): $t_R$=3.8 min, (M+H)⁺=338 (ES-API); IR: v=3196.15, 2926.11, 1660.77, 1489.10, 1091.75, 808.20, 736.83 cm⁻¹.

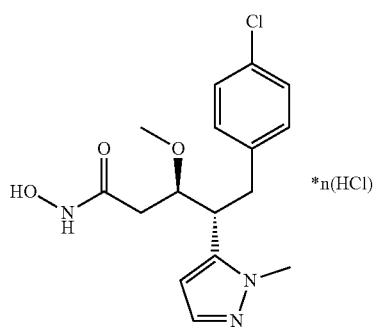 [SMILES: CO[C@H](CC(=O)NO)[C@H](Cc1ccc(Cl)cc1)c1ccnn1C]

(3R,4R)-5-(4-chlorophenyl)-N-hydroxy-3-methoxy-4-(1-methyl-M-pyrazol-3-yl)pentanamide hydrochloride salt (Compound 1-3): LC/MS (Method A): $t_R$=3.8 min, (M+H)⁺=338 (ES-API); IR: v=3189.40, 2931.90, 1652.09, 1494.88, 1403.26, 1099.46, 1015.56, 757.09 cm⁻¹

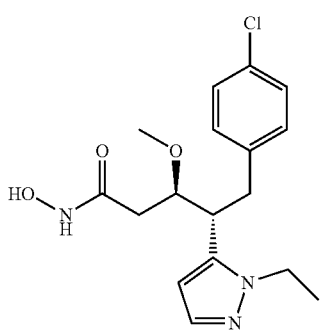 [SMILES: CCn1nccc1[C@@H](Cc1ccc(Cl)cc1)[C@@H](CC(=O)NO)OC]

(3R,4R)-5-(4-chlorophenyl)-4-(1-ethyl-1H-pyrazol-5-yl)-N-hydroxy-3-methoxypentanamide (Compound 1-4): LC/MS (Method A): $t_R$=4.1 min, (M+H)⁺=352 (ES-API); IR: v=3385.04, 2926.11, 1645.33, 1454.38, 1099.46, 1016.52, 806.27 cm⁻¹.

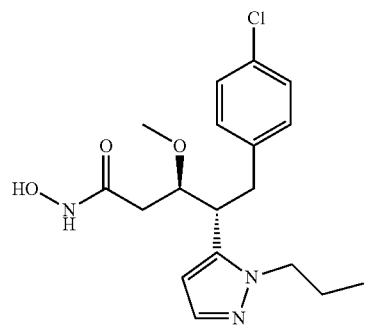 [SMILES: CCCn1nccc1[C@@H](Cc1ccc(Cl)cc1)[C@@H](CC(=O)NO)OC]

(3R,4R)-5-(4-chlorophenyl)-N-hydroxy-3-methoxy-4-(1-propyl-1H-pyrazol-5-yl)pentanamide (Compound 1-5): LC/MS (Method A): $t_R$=4.3 min, (M+H)⁺=366 (ES-API); IR: v=3217.37, 1651.12, 1489.10, 1408.08, 1095.60, 808.20, 738.76 cm⁻¹.

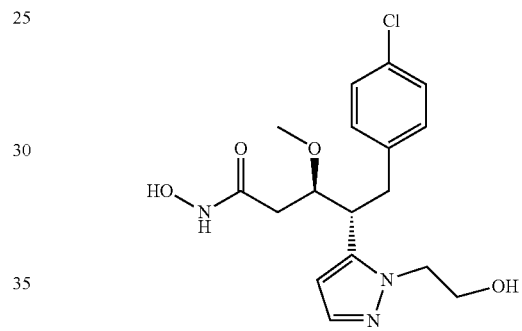

(3R,4R)-5-(4-chlorophenyl)-N-hydroxy-4-(1-(2-hydroxyethyl)-1H-pyrazol-5-yl)-3-methoxypentanamide (Compound 1-6): LC/MS (Method A): $t_R$=3.5 min, (M+H)⁺=368 (ES-API); IR: v=3367.11, 1654.98, 1491.02, 1410.01, 1097.53, 1014.59, 808.20, 786.98 cm⁻¹.

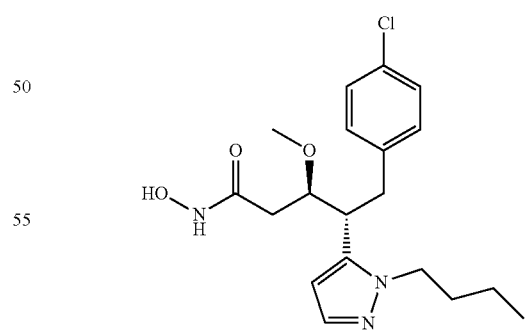

(3R,4R)-4-(1-butyl-1H-pyrazol-3-yl)-5-(4-chlorophenyl)-N-hydroxy-3-methoxypentanamide (Compound 1-7): LC/MS (Method A): $t_R$=4.7 min, (M+H)⁺=380 (ES-API); IR: v=3194.23, 2933.83, 1660.77, 1492.95, 1410.01, 1099.46, 808.20, 734.90 cm⁻¹.

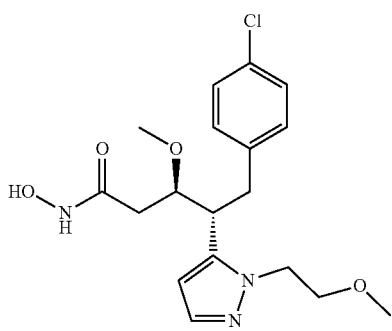 [SMILES: COCCn1nccc1[C@@H](Cc1ccc(Cl)cc1)[C@@H](CC(=O)NO)OC]

(3R,4R)-5-(4-chlorophenyl)-N-hydroxy-3-methoxy-4-(1-(2-methoxyethyl)-1H-pyrazol-5-yl)pentanamide (Compound 1-8): LC/MS (Method A): $t_R$=3.9 min, (M+H)$^+$=382 (ES-API); IR: v=3441.12, 2931.90, 1668.48, 1456.30, 1265.35, 1101.39, 738.76 cm$^{-1}$.

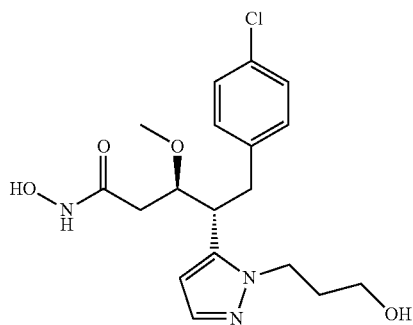 [SMILES: CO[C@H](CC(=O)NO)[C@H](Cc1ccc(Cl)cc1)c1ccnn1CCCO]

(3R,4R3R,4R)-5-(4-chlorophenyl)-N-hydroxy-4-(1-(3-hydroxypropyl)-1H-pyrazol-5-yl)-3-methoxypentanamide (Compound 1-9): LC/MS (Method A): $t_R$=3.6 min, (M+H)$^+$=382 (ES-API); IR: v=3352.39, 3211.59, 2926.11, 1666.55, 1487.17, 1097.53, 783.13 cm$^{-1}$.

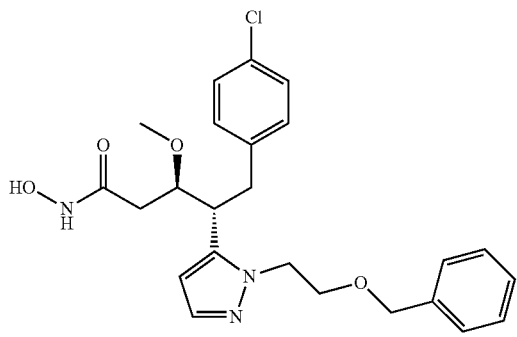 [SMILES: CO[C@H](CC(=O)NO)[C@H](Cc1ccc(Cl)cc1)c1ccnn1CCOCc1ccccc1]

(3R,4R)-4-(1-(2-(benzyloxy)ethyl)-1H-pyrazol-5-yl)-5-(4-chlorophenyl)-N-hydroxy-3-methoxypentanamide (Compound 1-10): LC/MS (Method A): $t_R$=5.1 min, (M+H)$^+$=458 (ES-API); IR: v=3350.11, 1666.55, 1487.17, 1454.38, 1099.48, 738.78, 698.25 cm$^{-1}$.

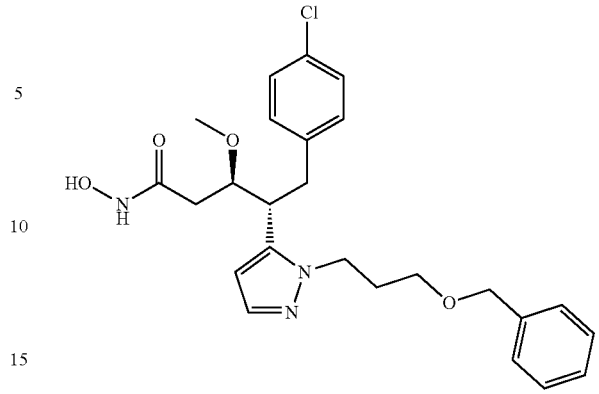

(3R,4R)-4-(1-(3-(benzyloxy)propyl)-1H-pyrazol-5-yl)-5-(4-chlorophenyl)-N-hydroxy-3-methoxypentanamide (Compound 1-11): LC/MS (Method A): $t_R$=5.0 min, (M+H)$^+$=472 (ES-API); IR: v=3344.68, 3207.73, 1666.55, 1454.38, 1099.46, 736.83 cm$^{-1}$.

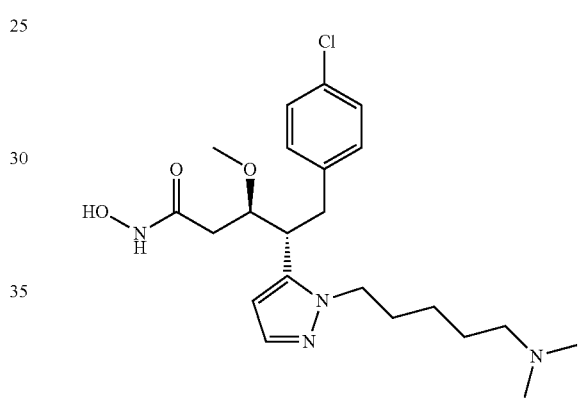

(3R,4R)-5-(4-chlorophenyl)-4-(1-(5-(dimethylamino)pentyl)-1H-pyrazol-5-yl)-N-hydroxy-3-methoxypentanamide (Compound 1-12): LC/MS (Method B): $t_R$=3.9 min, (M+H)$^+$=437 (ES-API); IR: v=3203.50, 2938.35, 1658.71, 1491.15, 1408.99, 1099.26, 1015.55, 750.07 cm$^{-1}$.

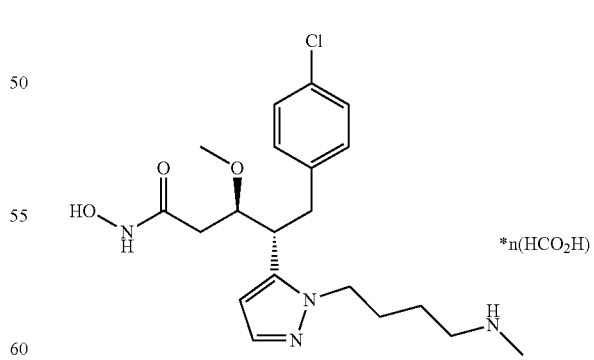

(3R,4R)-5-(4-chlorophenyl)-N-hydroxy-3-methoxy-4-(1-(4-(methylamino)butyl)-1H-pyrazol-5-yl)pentanamide formate salt (Compound 1-13): LC/MS (Method B): $t_R$=3.9 min, (M+H)$^+$=409 (ES-API); IR: v=3202.18, 1602.42, 1350.82, 1093.93, 762.35 cm$^{-1}$.

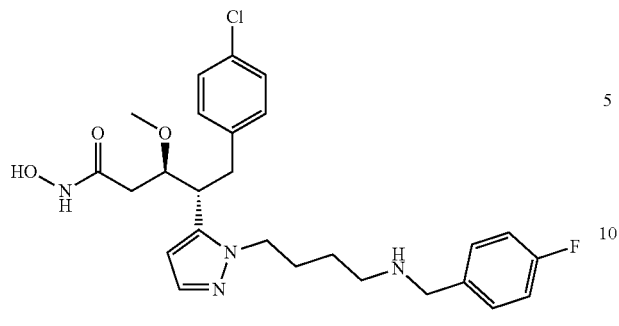

(3R,4R)-5-(4-chlorophenyl)-4-(1-(4-((4-fluorobenzyl)amino)butyl)-1H-pyrazol-5-yl)-N-hydroxy-3-methoxypentanamide, formate salt (Compound 1-14): LC/MS (Method B): $t_R$=4.3 min, (M+H)$^+$=503 (ES-API); IR: v=2937.35, 1603.11, 1513.84, 1351.75, 1226.59, 1099.84, 836.99, 771.90 cm$^{-1}$.

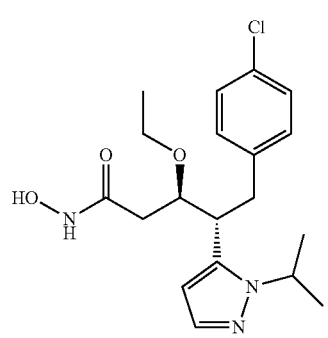

(3R,4R)-5-(4-chlorophenyl)-3-ethoxy-N-hydroxy-4-(1-isopropyl-1H-pyrazol-5-yl)pentanamide (Compound 2-2): LC/MS (Method A): $t_R$=4.5 min, (M+H)$^+$=380 (ES-API); IR: v=3174.23, 2931.83, 1660.77, 1491.95, 1410.01, 1099.46, 808.20, 731.84 cm$^{-1}$.

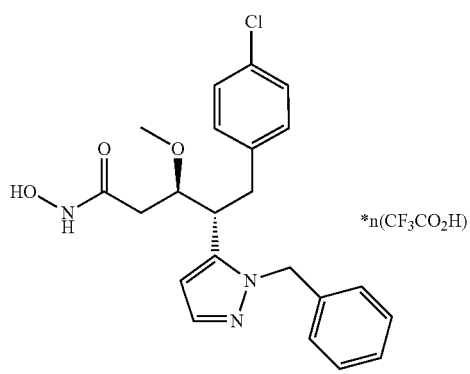 [SMILES: CO[C@H](CC(=O)NO)[C@H](Cc1ccc(Cl)cc1)c1ccnn1Cc1ccccc1]

(3R,4R)-4-(1-benzyl-1H-pyrazol-3-yl)-5-(4-chlorophenyl)-N-hydroxy-3-methoxypentanamide trifluoroacetate salt (Compound 1-15): LC/MS (Method A): $t_R$=4.9 min, (M+H)$^+$=414 (ES-API); IR: v=3309.96, 2827.74, 1664.62, 1492.95, 1082.10, 808.20, 717.54 cm$^{-1}$.

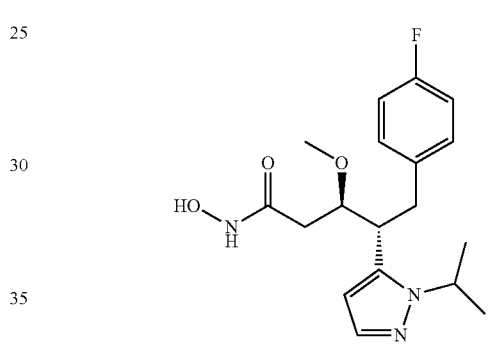

(3R,4R)-5-(4-fluorophenyl)-N-hydroxy-4-(1-isopropyl-M-pyrazol-5-yl)-3-methoxypentanamide (Compound 2-3): LC/MS (Method A): $t_R$=3.9 min, (M+H)$^+$=350 (ES-API); IR: v=3194.23, 2933.83, 1660.77, 1492.95, 1410.01, 1099.46, 808.20, 734.90 cm$^{-1}$.

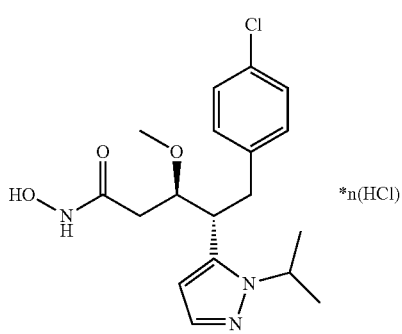 [SMILES: CO[C@H](CC(=O)NO)[C@H](Cc1ccc(Cl)cc1)c1ccnn1C(C)C]

(3R,4R)-5-(4-chlorophenyl)-N-hydroxy-4-(1-isopropyl-1H-pyrazol-5-yl)-3-methoxypentanamide hydrochloride salt (Compound 2-1): LC/MS (Method A): $t_R$=4.3 min, (M+H)$^+$=366; IR: v=3217.37, 2939.61, 1681.98, 1423.51, 1203.62, 800.49, 721.40 cm$^{-1}$.

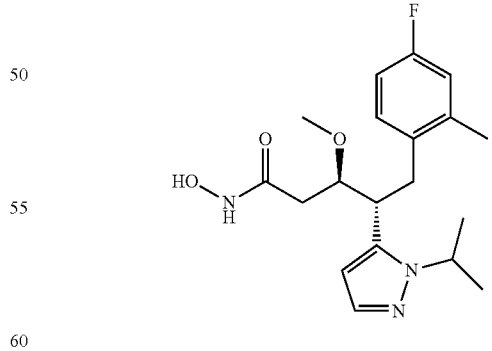

(3R,4R)-5-(4-fluoro-2-methylphenyl)-N-hydroxy-4-(1-isopropyl-1H-pyrazol-5-yl)-3-methoxypentanamide (Compound 2-4): LC/MS (Method A): $t_R$=4.2 min, (M+H)$^+$=364 (ES-API); IR: v=3194.23, 2933.83, 1660.77, 1492.95, 1410.01, 1099.46, 808.20, 734.90 cm$^{-1}$.

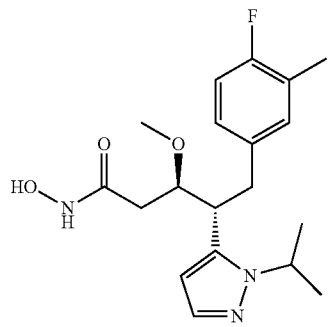 [SMILES: CO[C@H](CC(=O)NO)[C@H](Cc1ccc(F)c(C)c1)c1ccnn1C(C)C]

(3R,4R)-5-(4-fluoro-3-methylphenyl)-N-hydroxy-4-(1-isopropyl-1H-pyrazol-5-yl)-3-methoxypentanamide (Compound 2-5): LC/MS (Method A): $t_R$=4.2 min, (M+H)$^+$=364 (ES-API); IR: v=3194.23, 2933.83, 1660.77, 1492.95, 1410.01, 1099.46, 808.20, 734.90 cm$^{-1}$.

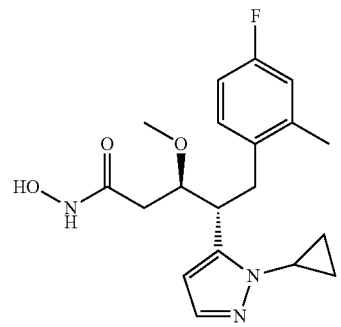

(3R,4R)-4-(1-cyclopropyl-1H-pyrazol-5-yl)-5-(4-fluoro-2-methylphenyl)-N-hydroxy-3-methoxypentanamide (Compound 3-2): LC/MS (Method A): $t_R$=4.1 min, (M+H)$^+$=362 (ES-API); IR: v=3298.58, 2934.17, 1702.49, 1511.97, 1246.52, 1161.32, 1031.37, 734.55 cm$^{-1}$.

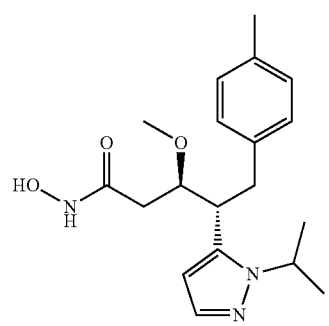 [SMILES: CO[C@H](CC(=O)NO)[C@H](Cc1ccc(C)cc1)c1ccnn1C(C)C]

(3R,4R)—N-hydroxy-4-(1-isopropyl-1H-pyrazol-5-yl)-3-methoxy-5-(p-tolyl)pentanamide (Compound 2-6): LC/MS (Method A): $t_R$=4.2 min, (M+H)$^+$=346 (ES-API); IR: v=3211.01, 1655.14, 1453.02, 1105.37, 781.62, 731.72, 553.12 cm$^{-1}$.

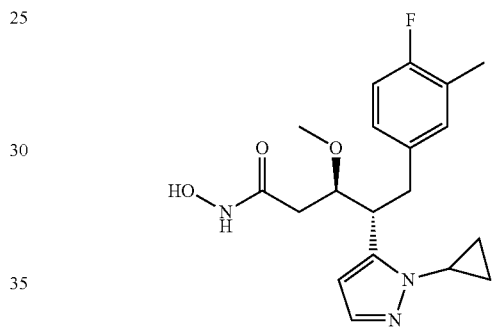

(3R,4R)-4-(1-cyclopropyl-1H-pyrazol-5-yl)-5-(4-fluoro-3-methylphenyl)-N-hydroxy-3-methoxypentanamide (Compound 3-3): LC/MS (Method A): $t_R$=4.1 min, (M+H)$^+$=362 (ES-API); IR: v=3194.23, 2933.83, 1660.77, 1492.95, 1410.01, 1099.46, 808.20, 734.90 cm$^{-1}$.

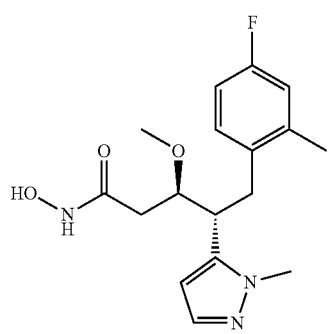 [SMILES: CO[C@H](CC(=O)NO)[C@H](Cc1ccc(F)cc1C)c1ccnn1C]

(3R,4R)-5-(4-fluoro-2-methylphenyl)-N-hydroxy-3-methoxy-4-(1-methyl-1H-pyrazol-5-yl)pentanamide (Compound 3-1): LC/MS (Method A): $t_R$=3.8 min, (M+H)$^+$=336 (ES-API); IR: v=3211.16, 2934.34, 1661.57, 1498.42, 1249.12, 1099.52, 587.07 cm$^{-1}$.

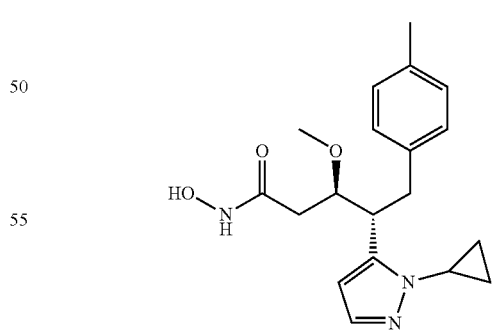

(3R,4R)-4-(1-cyclopropyl-1H-pyrazol-5-yl)-N-hydroxy-3-methoxy-5-(p-tolyl)pentanamide (Compound 3-4): LC/MS (Method A): $t_R$=4.1 min, (M+H)$^+$=344 (ES-API); IR: v=3377.58, 2924.19, 1667.29, 1514.68, 1405.51, 1107.33, 809.96, 735.32 cm$^{-1}$.

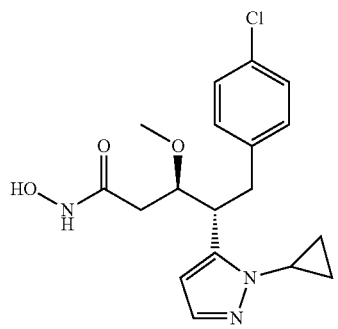 [SMILES: CO[C@H](CC(=O)NO)[C@H](Cc1ccc(Cl)cc1)c1ccnn1C1CC1]

(3R,4R)-5-(4-chlorophenyl)-4-(1-cyclopropyl-1H-pyrazol-5-yl)-N-hydroxy-3-methoxypentanamide (Compound 3-5): LC/MS (Method A): $t_R$=4.1 min, (M+H)$^+$=364 (ES-API); IR: v=3194.23, 2933.83, 1660.77, 1492.95, 1410.01, 1099.46, 808.20, 734.90 cm$^{-1}$.

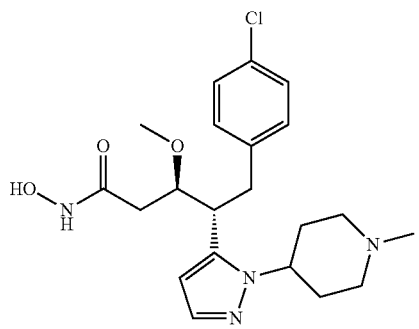

(3R,4R)-5-(4-chlorophenyl)-N-hydroxy-3-methoxy-4-(1-(1-methylpiperidin-4-yl)-1H-pyrazol-5-yl)pentanamide (Compound 3-8): LC/MS (Method A): $t_R$=2.9 min, (M+H)$^+$=421 (ES-API); IR: v=3346.61, 2916.47, 1651.12, 1454.38, 1263.42, 1101.39, 734.90 cm$^{-1}$.

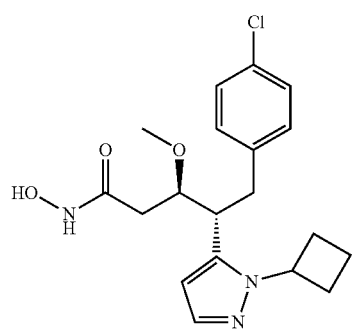 [SMILES: CO[C@H](CC(=O)NO)[C@H](Cc1ccc(Cl)cc1)c1ccnn1C1CCC1]

(3R,4R)-5-(4-chlorophenyl)-4-(1-cyclobutyl-1H-pyrazol-5-yl)-N-hydroxy-3-methoxypentanamide (Compound 3-6): LC/MS (Method A): $t_R$=4.5 min, (M+H)$^+$=378 (ES-API); IR: v=3443.05, 2916.47, 1662.69, 1448.59, 1265.35, 1101.39, 738.76 cm$^{-1}$.

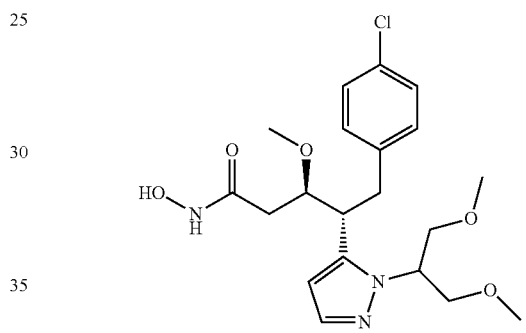

(3R,4R)-5-(4-chlorophenyl)-4-(1-(1,3-dimethoxypropan-2-yl)-1H-pyrazol-5-yl)-N-hydroxy-3-methoxypentanamide (Compound 3-9): LC/MS (Method A): $t_R$=4.3 min, (M+H)$^+$=426 (ES-API); IR: v=3443.05, 2916.47, 1662.69, 1448.59, 1265.35, 1101.39, 738.76 cm$^{-1}$.

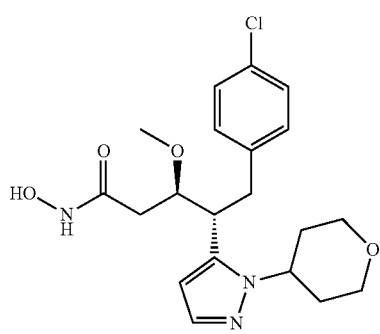 [SMILES: CO[C@H](CC(=O)NO)[C@H](Cc1ccc(Cl)cc1)c1ccnn1C1CCOCC1]

(3R,4R)-5-(4-chlorophenyl)-N-hydroxy-3-methoxy-4-(1-(tetrahydro-2H-pyran-4-yl)-1H-pyrazol-5-yl)pentanamide (Compound 3-7): LC/MS (Method A): $t_R$=4.3 min, (M+H)$^+$=408 (ES-API); IR: v=3176.87, 1653.05, 1487.17, 1290.42, 1099.46, 829.42, 732.97 cm$^{-1}$.

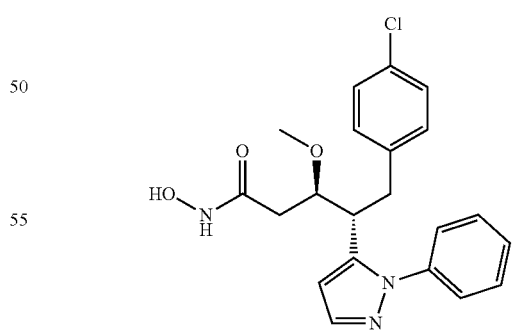

(3R,4R)-5-(4-chlorophenyl)-N-hydroxy-3-methoxy-4-(1-phenyl-1H-pyrazol-3-yl)pentanamide (Compound 3-10): LC/MS (Method A): $t_R$=5.2 min, (M+H)$^+$=400 (ES-API); IR: v=3217.37, 2931.80, 1651.12, 1525.74, 1384.94, 1093.67, 756.12 cm$^{-1}$.

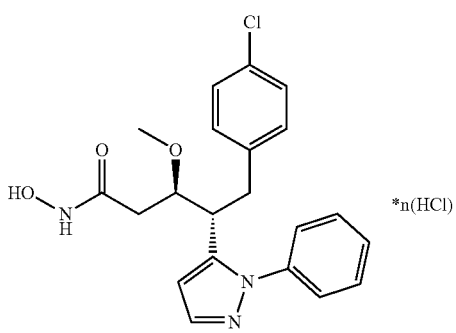 [SMILES: CO[C@H](CC(=O)NO)[C@H](Cc1ccc(Cl)cc1)c1ccnn1-c1ccccc1]

(3R,4R)-5-(4-chlorophenyl)-N-hydroxy-3-methoxy-4-(1-phenyl-1H-pyrazol-3-yl)pentanamide hydrochloride salt (Compound 3-11): LC/MS (Method A): $t_R$=5.2 min, (M+H)$^+$=400 (ES-API); IR: v=3217.37, 2931.80, 1651.12, 1525.74, 1384.94, 1093.67, 756.12 cm$^{-1}$.

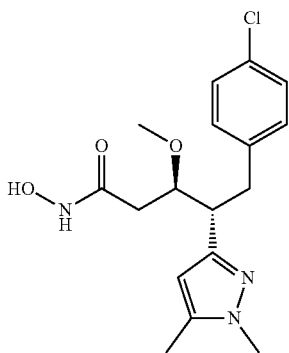 [SMILES: CO[C@H](CC(=O)NO)[C@H](Cc1ccc(Cl)cc1)c1cc(C)n(C)n1]

(3R,4R)-5-(4-chlorophenyl)-4-(1,5-dimethyl-1H-pyrazol-3-yl)-N-hydroxy-3-methoxypentanamide (Compound 4-1): LC/MS (Method B): $t_R$=4.8 min, (M+H)$^+$=352 (ES-API); IR: v=3196.15, 2935.76, 1660.77, 1645.33, 1489.10, 1384.94, 1091.75, 808.20 cm$^{-1}$.

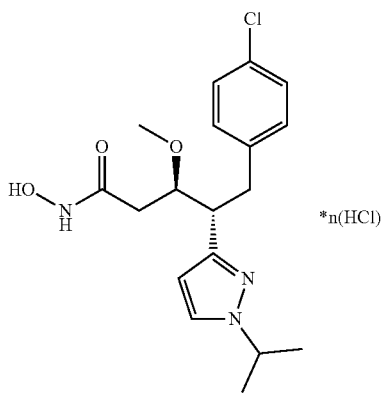 [SMILES: CO[C@H](CC(=O)NO)[C@H](Cc1ccc(Cl)cc1)c1ccn(C(C)C)n1]

(3R,4R)-5-(4-chlorophenyl)-N-hydroxy-4-(1-isopropyl-1H-pyrazol-3-yl)-3-methoxypentanamide hydrochloride salt (Compound 4-2): LC/MS (Method A): $t_R$=4.5 min, (M+H)$^+$=366 (ES-API); IR: v=3417.98, 3242.45, 1681.98, 1201.69, 1139.97, 806.27, 721.40 cm$^{-1}$.

Analytical Methods:

LC/MS spectra were recorded on a Shimadzu LC/MS-2020 DUIS with Nexera PDA and Sedex ELSD detectors and DUIS Electrospray (ESI+/−) ionization. The methods used were: (A) a solvent gradient beginning with 80% mobile phase A (mobile phase A=0.1% formic Acid in H$_2$O) and ending with 98% B (mobile phase B=0.1% formic acid in MeCN) at a flow rate of 1.0 mL/min with a run time of 11.0 minutes using a Zorbax XDB C18 (3.5 μm) column (4.6×75 mm); or (B) a solvent gradient beginning with 95% mobile phase A (mobile phase A=0.1% formic Acid in H$_2$O) and ending with 95% B (mobile phase B=0.1% formic Acid in MeCN) at a flow rate of 1.0 mL/min with a run time of 11.0 minutes using a Zorbax XDB C18 (3.5 μm) column (4.6×75 mm).

GC/MS was performed with a Shimadzu GC-2010 gas chromatography instrument coupled to a Shimadzu GC/MS-QP2010S mass spectrometer and a GC/MS Solution software Ver. 2.70 (Shimadzu). The method used was; (C) a SH-Rxi-5Sil MS column (30 m×0.25 mm i.d.) coated with 0.25 μm film 5% diphenyl/95% dimethylpolysiloxane was used for separation. Ultra High purity helium was used as carrier gas with flow-rate at 1.35 mL/min. The spectrometer was operated in electron-impact (EI) mode, the scan range was 40-600 amu, the ionization energy was 70 eV, and the scan rate was 0.5 s per scan. The ionization source temperature was 200° C. For each sample analysis, 3 μL was injected in split mode with a split ratio 20. The GC oven was initially heated isothermally at 200° C. held for 0.5 min, then increased to 330° C. (20° C./min) and held for 3 min at this final temperature.

IR spectra were recorded on a Shimadzu FTIR-8400S spectrometer.

NMR spectra were recorded on a Varian Unity Inova spectrometer.

TABLE 5

| ID | R$^1$ | R$^2$ | R$^3$ | K$_i$ (nM) |
|---|---|---|---|---|
| 5-1 | —OCH$_2$CH$_2$CH$_2$OH | 4-Cl | —iPr | 7.1 |
| 5-2 | —OCH$_2$CH$_2$CH$_3$ | 4-Cl | —iPr | 246 |
| 5-3 | —OCH$_2$CH(CH$_3$)$_2$ | 4-Cl | —iPr | 299 |
| 5-4 | —OCH$_2$CH$_2$CH$_2$F | 4-Cl | —iPr | 629 |
| 5-5 | —H | 4-Cl | —iPr | 7,450 |

Table B below summarizes additional abbreviations used in conjunction with the synthetic schemes below.

TABLE B

| (+)-(Ipc)$_2$B(allyl) | (+)-B-Allyldiisopinocampheylborane |
|---|---|
| A, Ala | Alanine |
| Abz | Aminobenzoic acid |
| amu | atomic mass unit |
| Ar | Argon |
| BOM | Benzyloxymethyl protecting group |
| C, Cys | Cysteine |
| CH$_3$CN, MeCN | acetonitrile |
| de | diastereomeric excess |
| D, Asp | Aspartic acid |

TABLE B-continued

| | |
|---|---|
| dARG | (D)-Arginine |
| DMF | N,N-dimethylformamide |
| DMP | Dess-Martin periodinane |
| Dnp | 2,4-dinitrophenyl protecting group |
| E, Glu | Glutamic acid |
| EDCI | 1-ethyl-3-(3-dimethylaminopropyl)carbodiimide |
| ELSD | evaporative light scattering detector |
| Et | Ethyl (—CH$_2$CH$_3$) |
| EtOAc | ethyl acetate |
| eV | electronvolt |
| F, Phe | Phenylalanine |
| G, Gly | Glycine |
| h | hours |
| H, His | Histidine |
| HEPES | 4-(2-hydroxyethyl)-1-piperazineethanesulfonic acid |
| HOBt | hydroxybenzotriazole |
| I, Ile | Isoleucine |
| iPr | Iso-propyl (—CH(CH$_3$)$_2$) |
| K, Lys | Lysine |
| KH$_2$PO$_4$ | Monopotassium phosphate |
| L, Leu | Leucine |
| LiBH$_4$ | lithium borohydride |
| M, Met | Methionine |
| Me | Methyl (—CH$_3$) |
| MeOH | methanol |
| mg | milligram |
| mm | millimeter |
| MOM | Methoxymethyl protecting group |
| n-BuLi | n-butyllithium |
| N, Asn | Asparagine |
| NaClO$_2$ | sodium chlorite |
| NaHCO$_3$ | sodium bicarbonate |
| NaHMDS | Sodium bis(trimethylsilyl)amide |
| NaOH | sodium hydroxide |
| Nle | norleucine |
| O$_3$ | ozone |
| P, Pro | Proline |
| PDA | photodiode array |
| Ph | Phenyl (—C$_6$H$_5$) |
| PPh$_3$ | triphenylphosphine |
| pyAOP | (7-Azabenzotriazol-1-yloxy)tripyrrolidinophosphonium hexafluorophosphate |
| Q, Gln | Glutamine |
| R, Arg | Arginine |
| RFU | Relative Fluorescence Unit |
| RP-HPLC | Reverse-Phase High Performance Liquid Chromatography |
| RT | room temperature |
| S, Ser | Serine |
| t-BuOH | tert-butanol |
| T, Thr | Threonine |
| TFA | Trifluoroacetic acid |
| TLC | Thin layer chromatography |
| V, Val | Valine |
| W, Trp | Tryptophan |
| Y, Tyr | Tyrosine |
| μL | microliter |
| μm | micrometer |

Synthesis of Exemplary Compounds-Scheme II

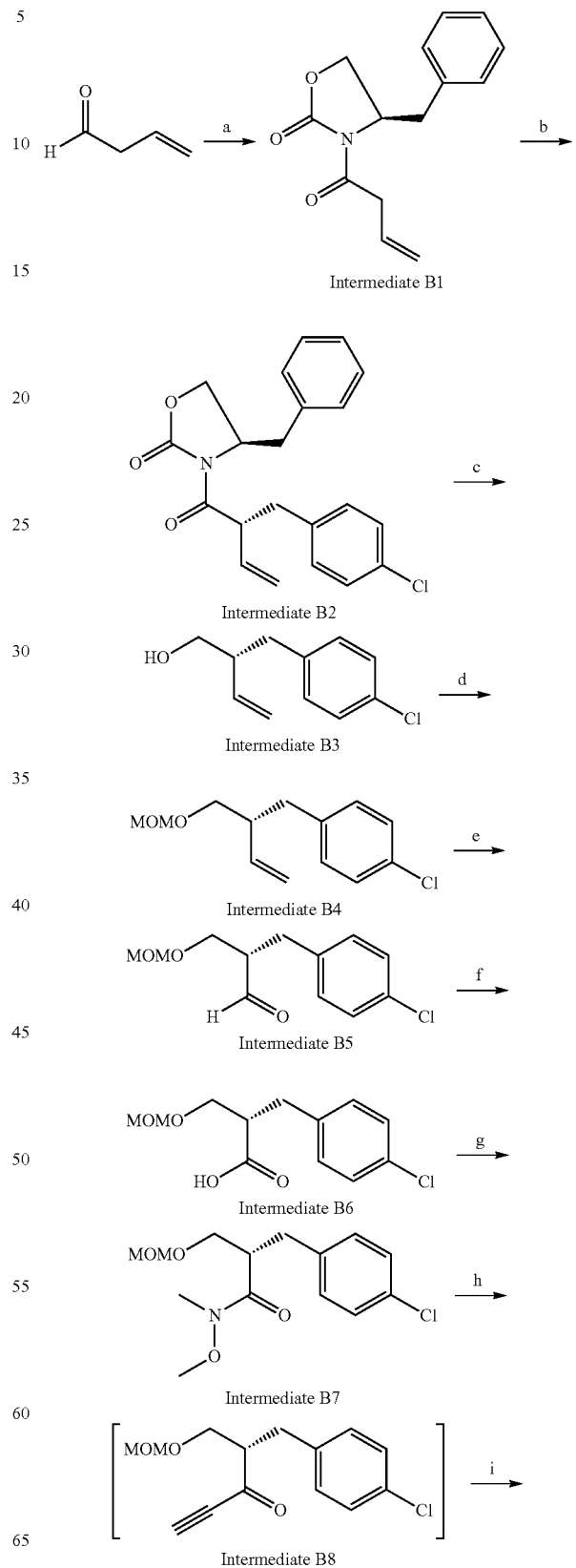

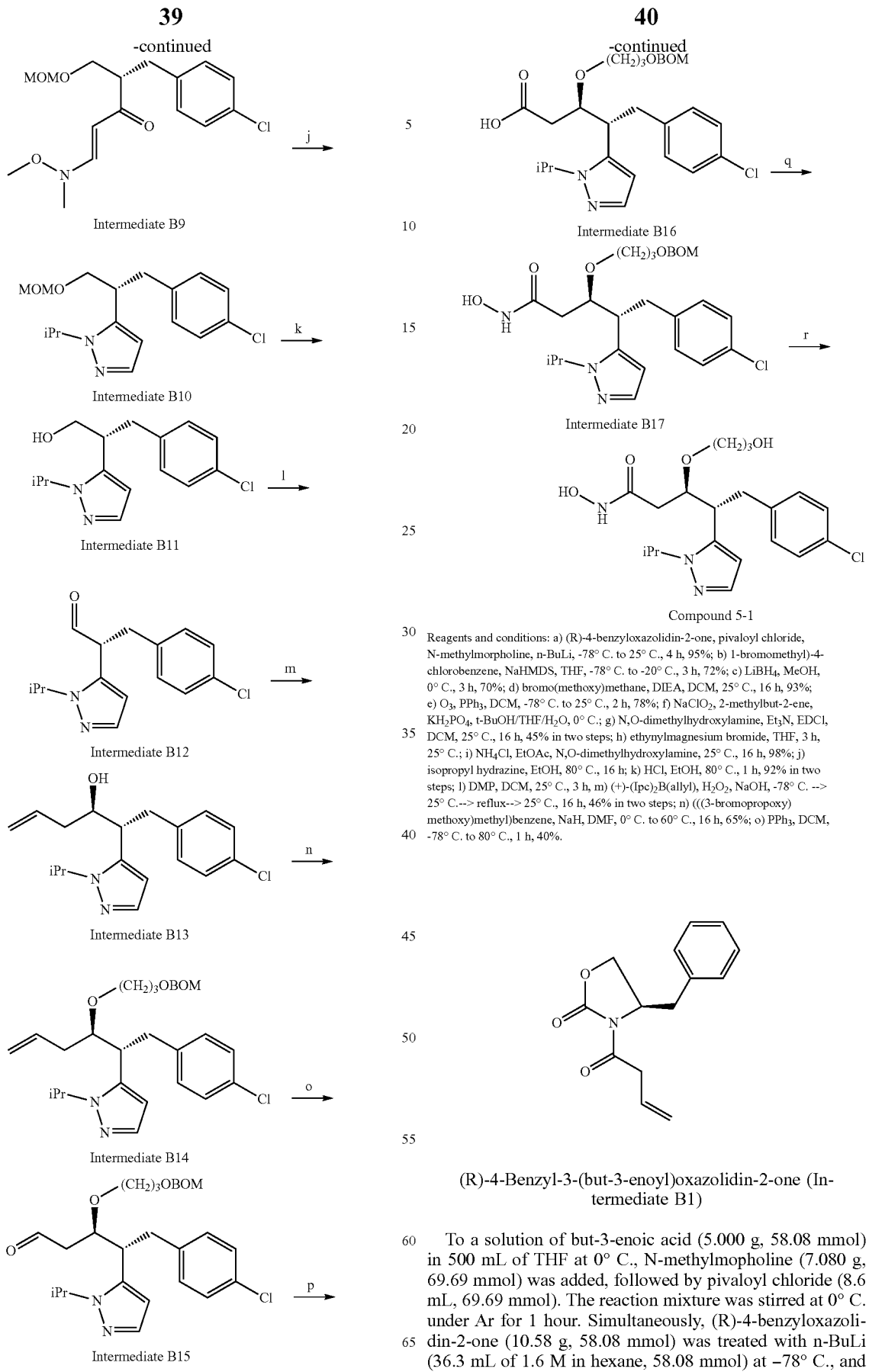

(R)-4-Benzyl-3-(but-3-enoyl)oxazolidin-2-one (Intermediate B1)

To a solution of but-3-enoic acid (5.000 g, 58.08 mmol) in 500 mL of THF at 0° C., N-methylmopholine (7.080 g, 69.69 mmol) was added, followed by pivaloyl chloride (8.6 mL, 69.69 mmol). The reaction mixture was stirred at 0° C. under Ar for 1 hour. Simultaneously, (R)-4-benzyloxazolidin-2-one (10.58 g, 58.08 mmol) was treated with n-BuLi (36.3 mL of 1.6 M in hexane, 58.08 mmol) at −78° C., and the mixture was stirred for 30 min at −78° C. To this mixture, the prepared anhydride was added and stirred for 1 hour at −78° C. The reaction mixture was slowly warmed to RT for a period of 4 hours. Saturated NH$_4$Cl was added (300 mL) and the mixture extracted with ethyl acetate (3×300 mL). The combined organic extracts were washed with brine (2×200 mL), dried over anhydrous, filtered, and concentrated under reduced pressure. The resulting residue was purified by column chromatography (silica gel) eluting with 5-30% ethyl acetate/hexanes to give the desired product as a colorless oil (13.5 g, 95.0% yield). GC/MS (Method D) purity 100%; $t_R$=5.6 min; M$^+$=245.

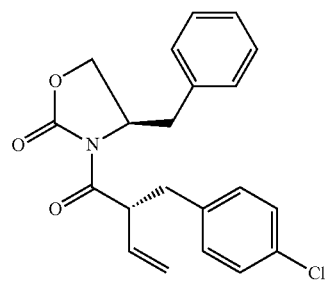 [SMILES: C=C[C@@H](Cc1ccc(Cl)cc1)C(=O)N1C(=O)OC[C@H]1Cc1ccccc1]

(R)-4-Benzyl-3-((R)-2-(4-chlorobenzyl)but-3-enoyl)oxazolidin-2-one (Intermediate B2)

To a solution of (R)-4-benzyl-3-(but-3-enoyl)oxazolidin-2-one (13.5 g, 55.0 mmol) in THF (300 mL) at −78° C. was added NaHMDS (66.0 mL, 1.0 M in THF, 66.0 mmol) dropwise and the resultant solution was stirred at −78° C. for 30 minutes. 1-(bromomethyl)-4-chlorobenzene (16.9 g, 82.5 mmol) was then added dropwise at −78° C. then allowed to warm and kept at −20° C. for 3 hours before being quenched with a saturated solution of NH$_4$Cl (200 mL). The crude reaction was extracted with EtOAc (3×200 mL), and the combined organic extracts were dried over anhydrous Na$_2$SO$_4$ and concentrated in vacuo after filtration. Purification by flash chromatography on silica gel, eluting with 0-20% EtOAc/hexanes, afforded 14.6 g (71.8%, 92% de) of the desired product as a white solid. GC/MS (Method D) purity 68%; $t_R$=7.5 min; M$^+$=369.

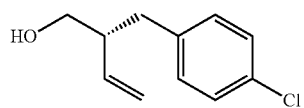

(R)-2-(4-Chlorobenzyl)but-3-en-1-ol (Intermediate B3)

A solution of (R)-4-benzyl-3-((R)-2-(4-chlorobenzyl)but-3-enoyl)oxazolidin-2-one (14.6 g, 39.5 mmol) in diethyl ether (400 mL) with 8.6 mL MeOH was added LiBH$_4$ (55.0 mL, 2.0 M in THF, 110 mmol) dropwise at 0° C. After stirring for three hours, the reaction was carefully quenched with a saturated solution of NH$_4$Cl (200 mL). The resulting mixture was extracted with diethyl ether (3×200 mL), and the combined organic extracts were washed with brine (2×200 mL), dried over anhydrous Na$_2$SO$_4$, and concentrated in vacuo after filtration. Purification by flash chromatography on silica gel, eluting with 2-30% EtOAc/hexanes, afforded 5.46 g (70.5%) of the desired product as a colorless oil. GC/MS (Method D) purity 100%; $t_R$=4.3 min; M$^+$=196, 125 (M$^+$-71) base peak.

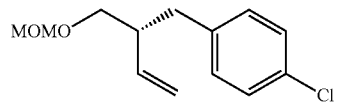

(R)-1-Chloro-4-(2-((methoxymethoxy)methyl)but-3-en-1-yl)benzene (Intermediate B4)

To a solution of (R)-2-(4-chlorobenzyl)but-3-en-1-ol (5.46 g, 27.9 mmol) in DCM (400 mL) at 25° C. was slowly added DIEA (12 mL, 69.6 mmol) and bromo(methoxy)methane (4.5 mL, 55.7 mmol). The reaction was stirred at 25° C. for 16 hours, then quenched by addition of saturated NH$_4$Cl (200 mL). The organic phase was separated and the aqueous phase was extracted with additional DCM (3×100 mL). The combined organic layers were washed with brine (3×100 mL) and dried over anhydrous Na$_2$SO$_4$. The solvent was evaporated under reduced pressure and the residue was purified by column chromatography on silica gel eluting with 0-15% EtOAc/hexanes to afford 6.24 g (93.2%) of the desired product as a colorless oil. GC/MS (Method D) purity 98%; $t_R$=4.6 min; M$^+$=240, 45 (M$^+$-195) base peak.

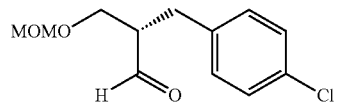

(S)-2-(4-Chlorobenzyl)-3-(methoxymethoxy)propanal (Intermediate B5)

A solution of (R)-1-chloro-4-(2-((methoxymethoxy)methyl)but-3-en-1-yl)benzene (4.1 g, 17 mmol) in DCM (200 mL) was cooled to −78° C. Then 0$_3$ was bubbled through the reaction solution until the solution turned blue, after which the reaction mixture was sparged with argon. Triphenylphosphine (9.0 g, 34 mmol) was added to the solution and the mixture was allowed to slowly warm to room temperature over one hour. After two hours of additional stirring at room temperature, the solution was concentrated under reduced pressure. The residue was purified by flash chromatography on silica gel eluting with 0-20% EtOAc/hexanes to afford 3.2 g (77.8%) of the desired product as a colorless oil. GC/MS (Method D) purity 100%; $t_R$=5.3 min; M$^+$=45 (M$^+$-197) base peak; IR (film) 2929, 2721, 1727, 1492, 1092, 1036, 840 cm$^{-1}$.

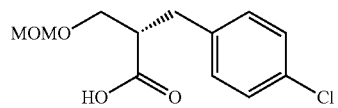

(S)-2-(4-Chlorobenzyl)-3-(methoxymethoxy)propanoic acid (Intermediate B6)

To a solution of (S)-2-(4-chlorobenzyl)-3-(methoxymethoxy)propanal (2.47 g, 10 mmol) in 59.6 mL t-BuOH and 22 mL THF with 2.5 g 2-methyl-2-butene was added a solution of NaClO$_2$ (3.6 g, 46.9 mmol) and KH$_2$PO$_4$ (4.6 g, 34 mmol) in 31.6 mL water at 0° C. The mixture was stirred for 3 hours at 0° C., then diluted with 100 mL water. The resulting mixture was extracted with EtOAc (3×75 mL) and the combined organic layers were washed with brine (2×50 mL). After drying over anhydrous Na$_2$SO$_4$ and filtration, the solvent was evaporated under reduced pressure and the residue was used in the next step without further purification. LC/MS (Method B): t$_R$=5.6 min, (M–H)$^+$=257 (API-ES); IR (film) 2941, 2892, 1732, 1711, 1493, 1037 cm$^{-1}$.

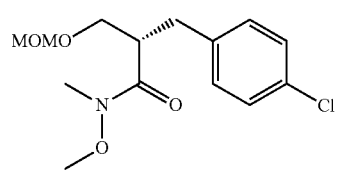

(S)-2-(4-Chlorobenzyl)-N-methoxy-3-(methoxymethoxy)-N-methylpropanamide (Intermediate B7)

To a solution of (S)-2-(4-chlorobenzyl)-3-(methoxymethoxy)propanoic acid from the previous reaction in 200 mL DCM was added N,O-dimethylhydroxylamine and HOBT. To the mixture was added Et$_3$N and EDCl followed by stirring for 16 hours at 25° C. The solvent was removed under reduced pressure and the residue was purified by flash chromatography on silica gel eluting with 0-10% MeOH/DCM to afford 1.3 g (45% in two steps) of the desired product as a colorless oil. LC/MS (Method A): purity 100%; t$_R$=5.4 min, (M+H)$^+$=302 (API-ES); GC/MS (Method D): purity 100%; t$_R$=6.6 min; M$^+$=301, 45 (M$^+$-256) base peak; IR (film) 2937, 2888, 2824, 1658, 1492, 1150, 1111 cm$^{-1}$.

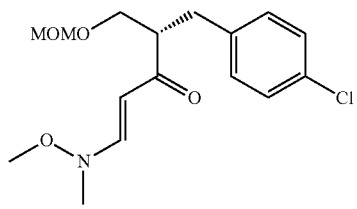

(S,E)-7-(4-Chlorobenzyl)-3-methyl-2,9,11-trioxa-3-azadodec-4-en-6-one (Intermediate B9)

To a solution of (S)-2-(4-chlorobenzyl)-N-methoxy-3-(methoxymethoxy)-N-methylpropanamide (1.3 g, 4.3 mmol) in 25 mL of THF, ethynylmagnesium bromide (30 mL of 0.5 M in THF, 15 mmol) was added. The reaction mixture was stirred at 25° C. for 3 hours, and then saturated NH$_4$Cl solution (34 mL) and ethyl acetate (13 mL) were added, followed by N,O-dimethylhydroxylamine hydrochloride (256 mg, 2.6 mmol). After stirring at room temperature for 16 hours, the layers were separated, and the aqueous layer was extracted with additional EtOAc (2×15 mL). The combined organic extracts were dried over anhydrous Na$_2$SO$_4$, filtered, and concentrated under reduced pressure. The resulting residue was purified by silica gel column chromatography eluting with 0-5% MeOH/DCM to give the desired product as an oil (1.4 g, 98% yield). LC/MS (Method A): purity 100%; t$_R$=5.3 min, (M+H)$^+$=328 (API-ES).

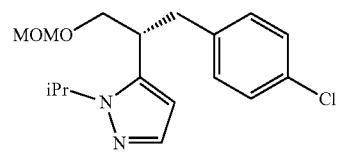

(R)-5-(1-(4-Chlorophenyl)-3-(methoxymethoxy) propan-2-yl)-1-isopropyl-1H-pyrazole (Intermediate B10)

To a solution of (S,E)-7-(4-chlorobenzyl)-3-methyl-2,9,11-trioxa-3-azadodec-4-en-6-one (2.5 g, 7.8 mmol) in 27 mL EtOH was added isopropyl hydrazine dihydrochloride (1.3 g, 11.6 mmol), and the reaction mixture was heated to 80° C. overnight. After cooling to room temperature, the reaction mixture was concentrated under reduced pressure and the residue was used for the next step without further purification. LC/MS (Method C): t$_R$=6.9 min, (M+H)$^+$=323 (API-ES).

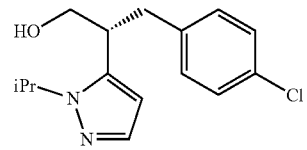 [SMILES: CC(C)n1nccc1[C@H](CO)Cc1ccc(Cl)cc1]

(R)-3-(4-Chlorophenyl)-2-(1-isopropyl-1H-pyrazol-5-yl)propan-1-ol (Intermediate B11)

To a crude solution of (R)-5-(1-(4-chlorophenyl)-3-(methoxymethoxy)propan-2-yl)-1-isopropyl-M-pyrazole in 27 mL EtOH was added conc. HCl (260 μL). The reaction mixture was heated to 80° C. and stirred for 1 hour. After cooling, the reaction mixture was rotary-evaporated under reduced pressure to a volume of about 5 mL. Saturated NaHCO$_3$ (30 mL) was added and the mixture extracted with EtOAc (3×30 mL). The combined organic layers were washed with brine (3×20 mL) and dried over Na$_2$SO$_4$. The solvent was evaporated under reduced pressure, and the residue was purified by flash chromatography on silica gel eluting with 0-7% MeOH/DCM to afford 2.6 g (92% in two steps) of the desired product as a colorless oil. LC/MS (Method A): t$_R$=4.9 min, (M+H)$^+$=279 (API-ES).

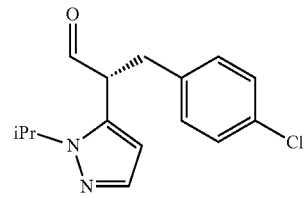 [SMILES: CC(C)n1nccc1[C@H](C=O)Cc1ccc(Cl)cc1]

(R)-3-(4-Chlorophenyl)-2-(1-isopropyl-1H-pyrazol-5-yl)propanal (Intermediate B12)

To a solution of (R)-3-(4-Chlorophenyl)-2-(1-isopropyl-M-pyrazol-5-yl)propan-1-ol (700 mg, 2.5 mmol) in DCM (35 mL) was added DMP (1.6 g, 3.8 mmol). The reaction mixture was stirred for 3 hours at 25° C. The reaction was added 5% NaHCO$_3$(50 mL) and extracted with more DCM (3×35 mL). The combined DCM layers were washed once with saturated NaHCO$_3$ and brine (2×20 mL) and dried over Na$_2$SO$_4$. After the solvent was evaporated under reduced pressure, the residue was used for the next step without further purification. LC/MS (Method A): t$_R$=5.8 min, (M+H)$^+$=277 (API-ES).

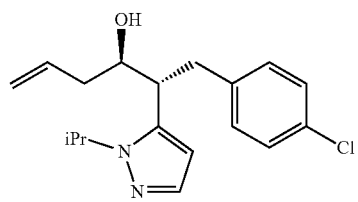 [SMILES: C=CC[C@@H](O)[C@H](Cc1ccc(Cl)cc1)c1ccnn1C(C)C]

(2R,3R)-1-(4-Chlorophenyl)-2-(1-isopropyl-1H-pyrazol-5-yl)hex-5-en-3-ol (Intermediate B13)

A solution of (R)-3-(4-chlorophenyl)-2-(1-isopropyl-1H-pyrazol-5-yl)propanal (300 mg, 1.1 mmol) in 25 mL ether/THF (1:4) was added (+)-(Ipc)$_2$B(allyl) (1.2 mL of 1 M in pentane, 1.2 mmol) at −78° C. The resulting mixture was vigorously stirred at −78° C. for three hours, and then allowed to warm to room temperature over three hours. The mixture was stirred for another 12 hours at this temperature. The reaction mixture was cooled to 0° C. and a premixed solution of 3N NaOH (1 mL) and 30% H$_2$O$_2$ (350 μL) was carefully added over 10 minutes. The resulting biphasic mixture was refluxed for two hours with vigorous stirring. The reaction mixture was cooled to room temperature, the organic phase was separated, and the aqueous phase was extracted with EtOAc (2×30 mL). The combined organic layers were washed with brine (2×30 mL), dried over Na$_2$SO$_4$, and filtered. The filtrate was concentrated under reduced pressure to give a light-yellow residue. This mixture was purified by flash chromatography eluting with 0-30% EtOAc/hexanes on silica gel to provide the allyl alcohol as a colorless oil (145 mg, 46% in two steps %). LC/MS (Method A): purity 100%; t$_R$=5.7 min, (M+H)$^+$=319 (API-ES).

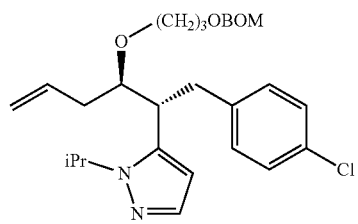

5-((2R,3R)-3-(3-((benzyloxy)methoxy)propoxy)-1-(4-chlorophenyl)hex-5-en-2-yl)-1-isopropyl-1H-pyrazole (Intermediate B14)

A solution of (2R,3R)-1-(4-chlorophenyl)-2-(1-isopropyl-1H-pyrazol-5-yl)hex-5-en-3-ol (58 mg, 0.18 mmol) in 2 mL DMF was cooled to 0° C. and sodium hydride was added (32 mg of 60% dispersion in mineral oil, 0.72 mmol). After stirring for five minutes, (((3-bromopropoxy)methoxy)methyl)benzene (162 mg, 0.64 mmol) was added and the reaction was allowed to warm to room temperature, and then heated to 60° C. After 16 hours, the reaction was cooled to room temperature and quenched with very slow addition of saturated NH$_4$Cl (15 mL). The resulting mixture was extracted with EtOAc (3×25 mL). The combined organic layers were washed with brine (2×15 mL) and dried over Na$_2$SO$_4$. Purification of the crude material via flash chromatography on silica gel (0-15% EtOAc/hexanes) afforded 58 mg (65%) of the ether as a light-yellow oil. LC/MS (Method A2): t$_R$=11.5 min, (M+H)$^+$=497 (API-ES).

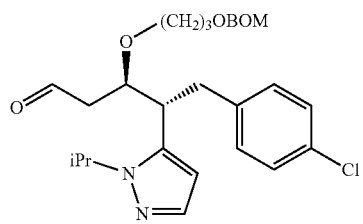

(3R,4R)-3-(3-((benzyloxy)methoxy)propoxy)-5-(4-chlorophenyl)-4-(1-isopropyl-1H-pyrazol-5-yl)pentanal (Intermediate B15)

A solution of 5-((2R,3R)-3-(3-((benzyloxy)methoxy)propoxy)-1-(4-chlorophenyl)hex-5-en-2-yl)-1-isopropyl-1H-pyrazole (49.4 mg, 0.10 mmol) in DCM (5 mL) was cooled to −78° C., and O$_3$ was bubbled through until the solution turned blue. The reaction mixture was then sparged with argon. Triphenylphosphine (52.4 mg, 0.20 mmol) was added, and the solution was allowed to warm slowly to room temperature over one hour. After two hours of additional stirring at room temperature, the solution was concentrated in vacuo. The residue was purified by flash chromatography on silica gel eluting with 0-40% EtOAc/hexanes to afford 49 mg (99%) of the desired product as a light-yellow oil. TLC on silica: R$_f$=0.21 (20% EtOAc/hexane); IR (film) 2399, 2725, 1722, 1677, 1492, 1094, 4046, 739, 699 cm$^{-1}$.

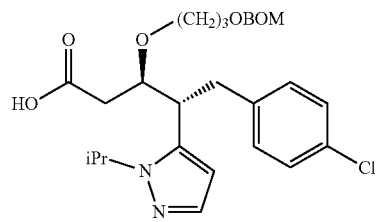

(3R,4R)-3-(3-((benzyloxy)methoxy)propoxy)-5-(4-chlorophenyl)-4-(1-isopropyl-1H-pyrazol-5-yl)pentanoic acid (Intermediate B16)

To a solution of (3R,4R)-3-(3-((benzyloxy)methoxy)propoxy)-5-(4-chlorophenyl)-4-(1-isopropyl-1H-pyrazol-5-yl)pentanal (49 mg, 0.10 mmol) in 488 μL t-BuOH and 180 μL THF with 21 mg 2-methyl-2-butene was added NaClO$_2$ (34 mg, 0.38 mmol) in 259 μL water with KH$_2$PO$_4$ (38 mg, 0.28 mmol) at 0° C. The mixture was stirred for 3 hours at 0° C. and diluted with 10 mL water. The mixture was extracted with EtOAc (3×10 mL) and the combined organic layers were washed with brine (2×5 mL). After dried over anhydrous Na$_2$SO$_4$ and filtered, the solvent was evaporated under reduced pressure and the residue was used for the next step without further purification.

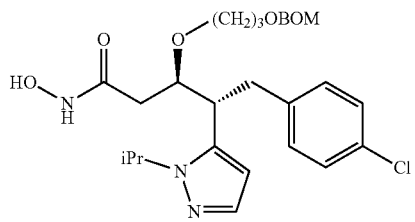

(3R,4R)-3-(3-((benzyloxy)methoxy)propoxy)-5-(4-chlorophenyl)-N-hydroxy-4-(1-isopropyl-1H-pyrazol-5-yl)pentanamide (Intermediate B17)

To a 0° C. solution of (3R,4R)-3-(3-((benzyloxy)methoxy)propoxy)-5-(4-chlorophenyl)-4-(1-isopropyl-1H-pyrazol-5-yl)pentanoic acid in 2 mL DMF was added NH$_2$OH·HCl (17 mg, 0.25 mmol), pyAOP (78 mg, 0.15 mmol), and DIEA (68 μL, 0.39 mmol). After stirring for 6 hours, the reaction was quenched with addition of saturated NH$_4$Cl (5 mL). The resulting mixture was extracted with DCM (3×10 mL). The combined DCM layers were washed with brine (2×5 mL) and dried over Na$_2$SO$_4$. Purification of the crude material via flash chromatography on amine-based silica gel (0-15% DCM/hexanes) afforded 37 mg (69%) of the ether as an oil. LC/MS (Method B): purity 100%; t$_R$=6.4 min, (M+H)$^+$=530 (API-ES); IR (dry film) 3196, 2932, 2875, 1659, 1492, 1093 cm$^{-1}$.

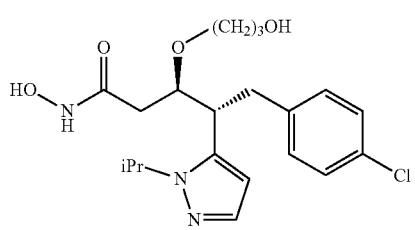

(3R,4R)-5-(4-chlorophenyl)-N-hydroxy-3-(3-hydroxypropoxy)-4-(1-isopropyl-1H-pyrazol-5-yl)pentanamide (Compound 5-1)

To a solution of (3R,4R)-3-(3-((benzyloxy)methoxy)propoxy)-5-(4-chlorophenyl)-N-hydroxy-4-(1-isopropyl-1H-pyrazol-5-yl)pentanamide (10 mg, 0.02 mmol) in 1.2 mL of THF-dioxane (1:2) was added conc. HCl (400 μL). The reaction mixture was heated to 80° C. and stirred for 1 hour. After cooling, the reaction mixture was rotary evaporated under reduced pressure to a volume of about 5 mL. Saturated NaHCO$_3$ (5 mL) was added the mixture extracted with DCM (3×7 mL). The combined organic layers were washed with brine (3×5 mL) and dried over Na$_2$SO$_4$. The solvent was evaporated under reduced pressure, and the residue was purified by RP-HPLC eluting with 80% to 2% CH$_3$CN/H$_2$O with 0.1% formic acid to give the title compound, 3.3 mg (43%), as an off-white solid. LC/MS (Method B): purity 100%; t$_R$=4.8 min, (M+H)$^+$=410 (API-ES); IR (dry film) 3205, 2979, 2931, 2880, 1661, 1490, 1411, 1093, 1017 cm$^{-1}$.

Characterizing Data for Additional Exemplary Compounds

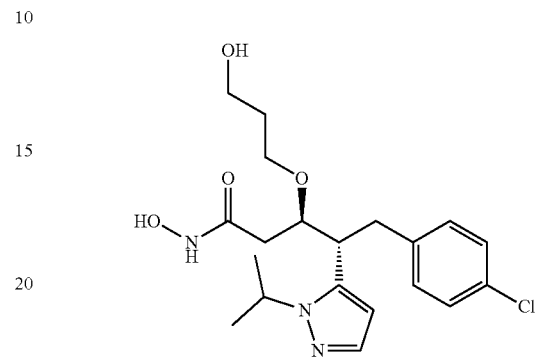

(3R,4R)-5-(4-chlorophenyl)-N-hydroxy-3-(3-hydroxypropoxy)-4-(1-isopropyl-M-pyrazol-5-yl)pentanamide (Compound 5-1): LC/MS (Method B): purity 100%; t$_R$=4.8 min, (M+H)$^+$=410 (API-ES); IR (dry film) 3205, 2979, 2931, 2880, 1661, 1490, 1411, 1093, 1017 cm$^{-1}$.

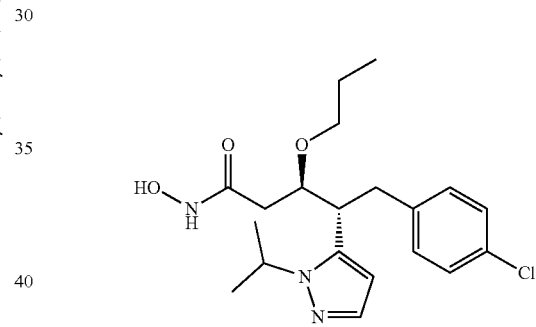

(3R,4R)-5-(4-chlorophenyl)-N-hydroxy-4-(1-isopropyl-M-pyrazol-5-yl)-3-propoxypentanamide (Compound 5-2): LC/MS (Method B): purity 100%; t$_R$=5.7 min, (M+H)$^+$=394 (API-ES); IR (dry film) 3182, 2971, 2934, 2872, 1658, 1492, 1410, 1092, 1015, 807 cm$^{-1}$.

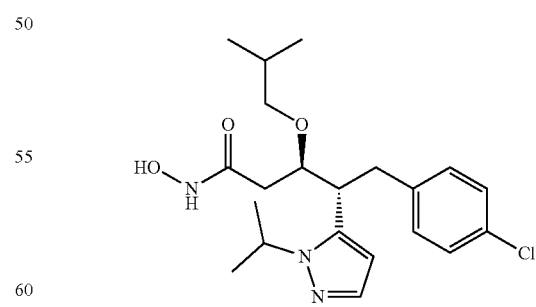

(3R,4R)-5-(4-chlorophenyl)-N-hydroxy-3-isobutoxy-4-(1-isopropyl-M-pyrazol-5-yl)pentanamide (Compound 5-3): LC/MS (Method B): purity 100%; t$_R$=6.1 min, (M+H)$^+$=408 (API-ES); IR (dry film) 3186, 2959, 2927, 2872, 1655, 1491, 1410, 1250, 1092, 1016, 808 cm$^{-1}$.

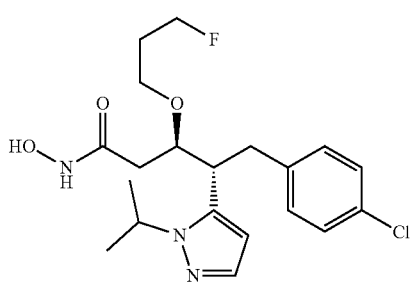 [SMILES: CC(C)n1nccc1[C@@H](Cc1ccc(Cl)cc1)[C@@H](CC(=O)NO)OCCCF]

(3R,4R)-5-(4-chlorophenyl)-3-(3-fluoropropoxy)-N-hydroxy-4-(1-isopropyl-1H-pyrazol-5-Apentanamide (Compound 5-4): LC/MS (Method B): purity 100%; $t_R$=5.5 min, $(M+H)^+$=411 (API-ES); IR (dry film) 3184, 2975, 2924, 2876, 1658, 1491, 1368, 1249, 1206, 1091, 1015, 701 cm$^{-1}$.

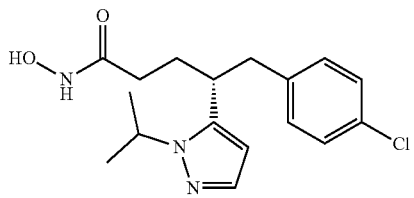 [SMILES: CC(C)n1nccc1[C@H](CCC(=O)NO)Cc1ccc(Cl)cc1]

(R)-5-(4-chlorophenyl)-N-hydroxy-4-(1-isopropyl-1H-pyrazol-5-yl)pentanamide (Compound 5-5): LC/MS (Method B): purity 96%; $t_R$=4.2 min, $(M+H)^+$=336 (API-ES); IR (dry film) 3197, 2983, 2932, 2864, 1651, 1492, 1411, 1093, 1013 cm$^{-1}$.

Additional Analytical Methods:

LC/MS conditions, Method (A2): LC/MS spectra were recorded on a Shimadzu LC/MS-2020 DUIS with Nexera PDA and Sedex ELSD detectors and DUIS (dual ion source) Electrospray (ESI+/−) ionization. Method (A2) utilized a solvent gradient beginning with 80% mobile phase A (mobile phase A=0.1% formic acid in H$_2$O) and ending with 98% B (mobile phase B=0.1% formic acid in MeCN) at a flow rate of 1.0 mL/min with a run time of 15.0 minutes using a Zorbax XDB C18 (3.5 μm) column (4.6×75 mm).

GC/MS conditions, Method (D). GC/MS was performed with a Shimadzu GC-2010 gas chromatography instrument coupled to a Shimadzu GCMS-QP2010S mass spectrometer and a GCMS Solution software Ver. 2.70 (Shimadzu). Method (D) utilized a SH-Rxi-5Sil MS column (30 m×0.25 mm i.d.) coated with 0.25 μm film 5% diphenyl/95% dimethylpolysiloxane for separation. Ultra High purity helium was used as carrier gas with flow-rate at 1.46 mL/min. The spectrometer was operated in electron-impact (EI) mode, the scan range was 40-600 amu, the ionization energy was 70 eV, and the scan rate was 0.35 s per scan. The ionization source temperature was 200° C. For each sample analysis, 3 μL was injected in split mode with a Split ratio 4.0. The GC oven was initially heated isothermally at 100° C. held for 1 min, then increased to 320° C. (35° C./min) and held for 10 min at this final temperature.

---

What is claimed is:

1. A compound of Formula I or pharmaceutically acceptable salt

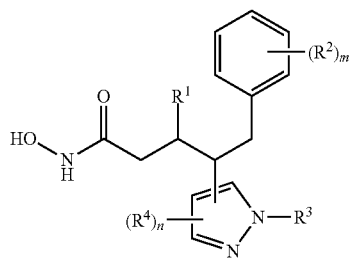

I thereof:
wherein $R^1$ is —$OR^5$;
m is an integer from 0 to 5;
n is an integer from 0 to 2;
each $R^2$ is independently selected from the group consisting of hydrogen, halogen, and alkyl;
$R^3$ is selected from the group consisting of hydrogen, alkyl, cycloalkyl, aryl, hydroxyalkyl, alkoxyalkyl, aryloxyalkyl, aralkyloxyalkyl, aralkyl, alkylaminoalkyl, dialkylaminoalkyl, aralkylaminoalkyl, and heterocycloalkyl,
each $R^4$ is independently hydrogen or alkyl;
$R^5$ is an alkyl; and
each of $R^2$, $R^3$, $R^4$, and $R^5$ being independently optionally substituted.

2. The compound of claim 1, wherein $R^5$ is an unsubstituted lower alkyl having from 1 to 6 carbons.

3. The compound of claim 1, wherein $R^5$ is a lower alkyl having from 1 to 6 carbons substituted with one or more OH, and/or halogen.

4. The compound of claim 1, wherein $R^5$ is selected from the group consisting of methyl, ethyl, n-propyl, isobutyl, —$CH_2CH_2CH_2OH$, and —$CH_2CH_2CH_2F$.

5. The compound of claim 1, wherein $R^2$ is methyl, chlorine, or fluorine.

6. The compound of claim 1, wherein $R^3$ is selected from the group consisting of methyl, ethyl, isopropyl, n-propyl, cyclopropyl, n-butyl, cyclobutyl, phenyl, and benzyl.

7. The compound of claim 1, wherein $R^3$ is isopropyl.

8. The compound of claim 1, wherein $R^3$ is of formula —$(CH_2)_yXR_z$;
wherein y is an integer from 2 to 5;
z is 1 or 2;
X is O or N;
each R is independently selected from the group consisting of hydrogen, methyl, and optionally substituted benzyl.

9. The compound of claim 1, wherein $R^3$ is selected from the group consisting of pyran-4-yl, 1-N-Me-piperidin-4-yl, and —$CH(CH_2OMe)_2$.

10. The compound of claim 1, wherein a salt form is selected from the group consisting of a hydrochloric acid salt, a formic acid salt, and a trifluoroacetic acid salt.

11. The compound of claim 1, wherein $R^5$ is methyl, $R^2$ is 4-chloro, $R^3$ is isopropyl, and $R^4$ is hydrogen.

12. A compound of Formula II or pharmaceutically acceptable salt thereof:

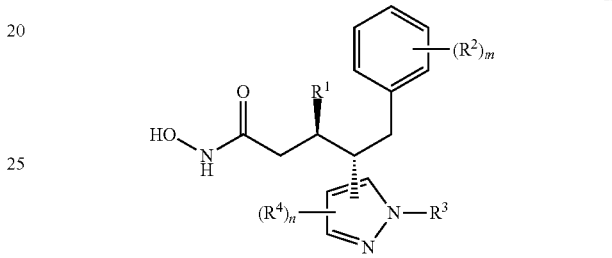

II wherein $R^1$ is —$OR^5$;
m is an integer from 0 to 5;
n is an integer from 0 to 2;
each $R^2$ is independently selected from the group consisting of hydrogen, halogen, and alkyl;
$R^3$ is selected from the group consisting of hydrogen, alkyl, cycloalkyl aryl, hydroxyalkyl, alkoxyalkyl, aryloxyalkyl, aralkyloxyalkyl, aralkyl, alkylaminoalkyl, dialkylaminoalkyl, aralkylaminoalkyl, and heterocycloalkyl,
each $R^4$ is independently hydrogen or alkyl;
$R^5$ is an alkyl; and
each of $R^2$, $R^3$, $R^4$, and $R^5$ being independently optionally substituted with hydroxy, alkoxy, halogen, or alkyl.

13. The compound of claim 12, wherein $R^5$ is selected from the group consisting of methyl, ethyl, n-propyl, isobutyl, —$CH_2CH_2CH_2OH$, and —$CH_2CH_2CH_2F$.

14. The compound of claim 12, wherein $R^2$ is methyl, chlorine, or fluorine.

15. The compound of claim 12, wherein $R^3$ is selected from the group consisting of methyl, ethyl, isopropyl, n-propyl, cyclopropyl, n-butyl, cyclobutyl, phenyl, and benzyl.

16. The compound of claim 12, wherein $R^3$ is isopropyl.

17. The compound of claim 12, wherein $R^3$ is of formula —$(CH_2)_yXR_z$;
wherein y is an integer from 2 to 5;
z is 1 or 2;
X is O or N; and
each R is independently selected from the group consisting of hydrogen, methyl, and optionally substituted benzyl.

18. The compound of claim 12, wherein $R^3$ is selected from the group consisting of pyran-4-yl, 1-N-Me-piperidin-4-yl, and —$CH(CH_2OMe)_2$.

19. The compound of claim 12, wherein a salt form is selected from the group consisting of a hydrochloric acid salt, a formic acid salt, and a trifluoroacetic acid salt.

20. The compound of claim 12, wherein $R^5$ is methyl, $R^2$ is 4-chloro, $R^3$ is isopropyl, and $R^4$ is hydrogen.

21. A compound of formula III or pharmaceutically acceptable salt thereof:

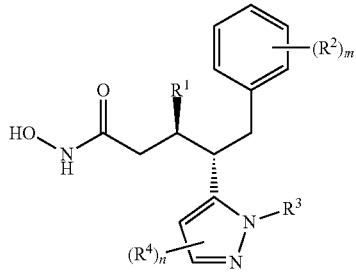

wherein $R^1$ is —$OR^5$;

m is an integer from 0 to 5;

n is an integer from 0 to 2;

each $R^2$ is independently selected from the group consisting of hydrogen, halogen, and alkyl;

$R^3$ is selected from the group consisting of hydrogen, alkyl, cycloalkyl aryl, hydroxyalkyl, alkoxyalkyl, aryloxyalkyl, aralkyloxyalkyl, aralkyl, alkylaminoalkyl, dialkylaminoalkyl, aralkylaminoalkyl, and heterocycloalkyl, each $R^4$ is independently hydrogen or alkyl;

$R^5$ is an alkyl; and each of $R^2$, $R^3$, $R^4$, and $R^5$ being independently optionally substituted with hydroxy, alkoxy, halogen, or alkyl.

22. The compound of claim 21, wherein $R^5$ is selected from the group consisting of methyl, ethyl, n-propyl, isobutyl, —$CH_2CH_2CH_2OH$, and —$CH_2CH_2CH_2F$.

23. The compound of claim 21, wherein $R^2$ is methyl, chlorine, or fluorine.

24. The compound of claim 21, wherein $R^3$ is selected from the group consisting of methyl, ethyl, isopropyl, n-propyl, cyclopropyl, n-butyl, cyclobutyl, phenyl, and benzyl.

25. The compound of claim 21, wherein $R^3$ is isopropyl.

26. The compound of claim 21, wherein $R^3$ is of formula —$(CH_2)_yXR_z$;

wherein y is an integer from 2 to 5;

z is 1 or 2;

X is O or N;

each R is independently selected from the group consisting of hydrogen, methyl, and optionally substituted benzyl.

27. The compound of claim 21, wherein $R^3$ is selected from the group consisting of pyran-4-yl, 1-N-Me-piperidin-4-yl, and —$CH(CH_2OMe)_2$.

28. The compound of claim 21, wherein a salt form is selected from the group consisting of a hydrochloric acid salt, a formic acid salt, and a trifluoroacetic acid salt.

29. The compound of claim 21, wherein $R^5$ is methyl, $R^2$ is 4-chloro, $R^3$ is isopropyl, and $R^4$ is hydrogen.

30. A compound selected from any one of the following structures:

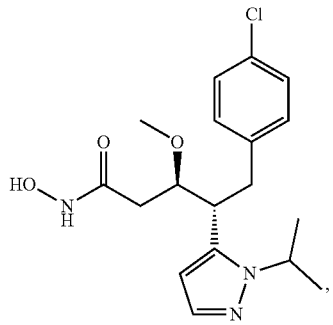
1-1

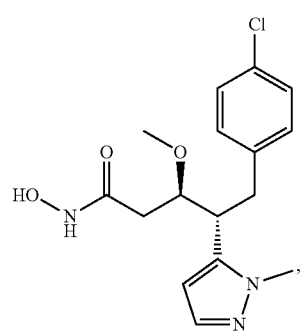
1-2

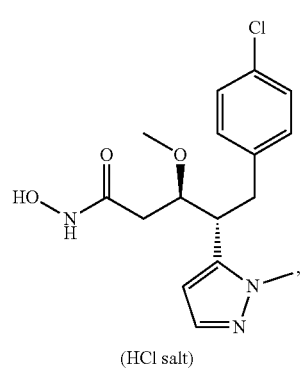
1-3
(HCl salt)

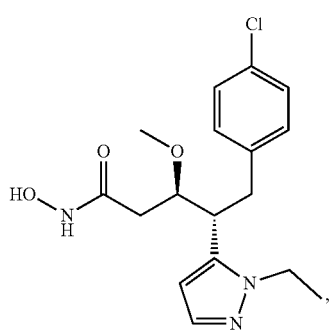
1-4

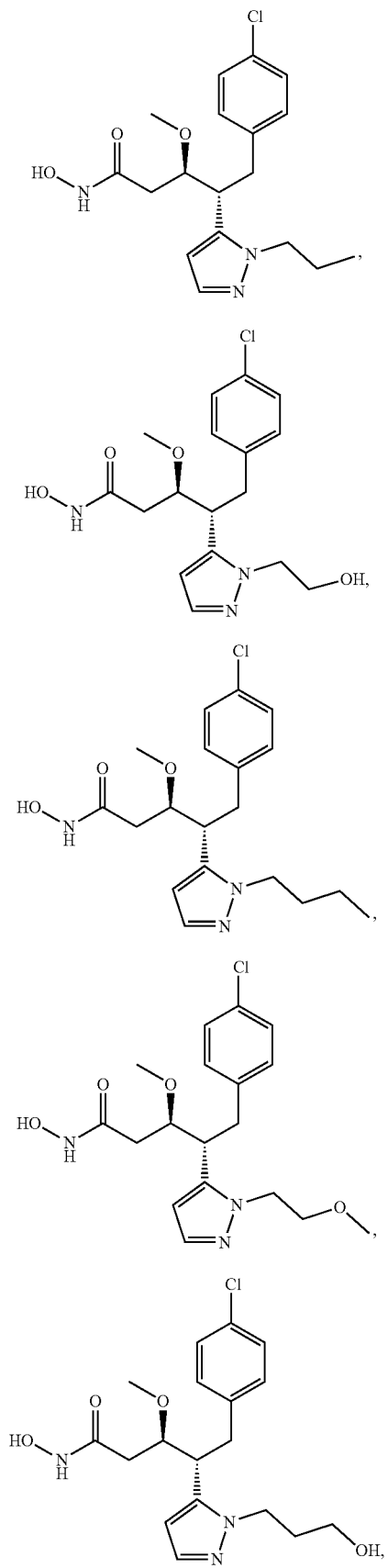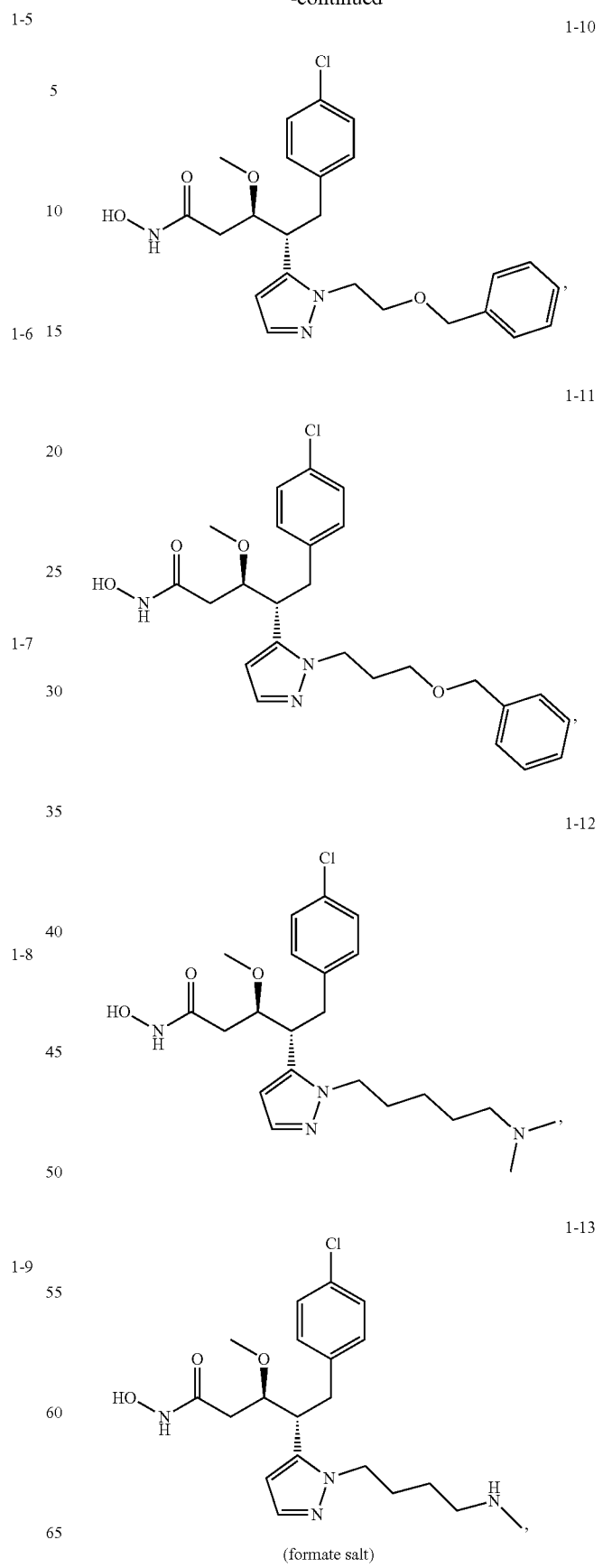

-continued
1-14
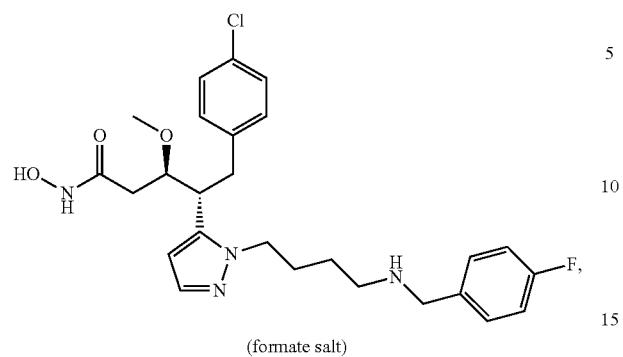
(formate salt)
1-15
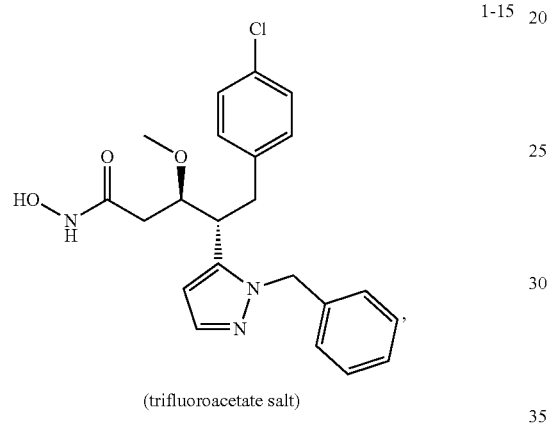
(trifluoroacetate salt)
2-1
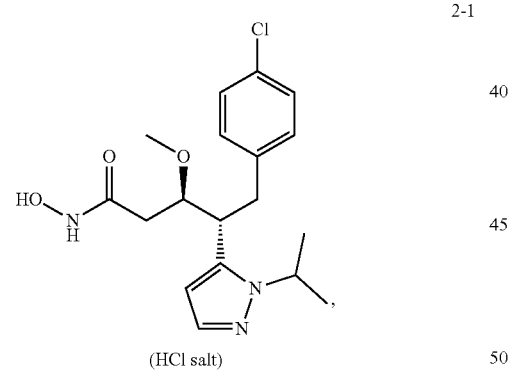
(HCl salt)
2-2
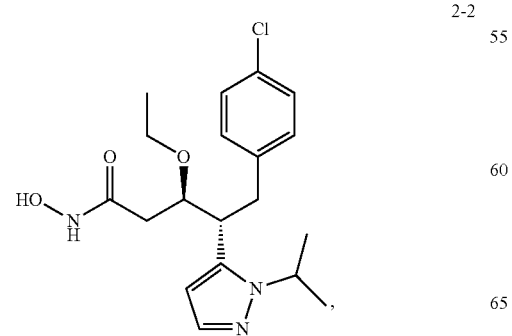
-continued
2-3
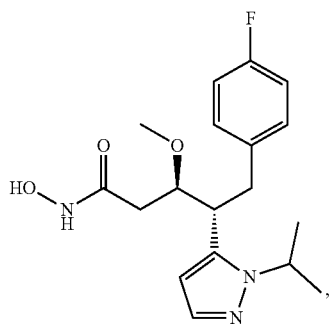
2-4
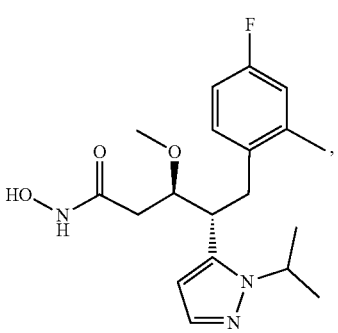
2-5
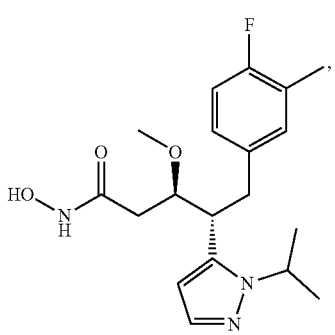
2-6
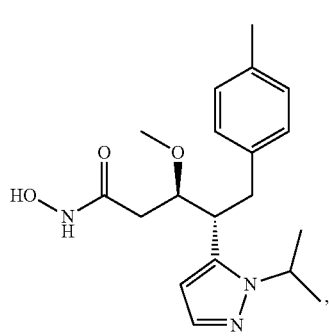
3-1
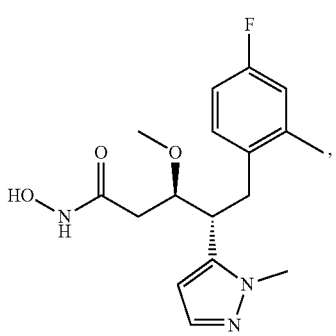

3-2
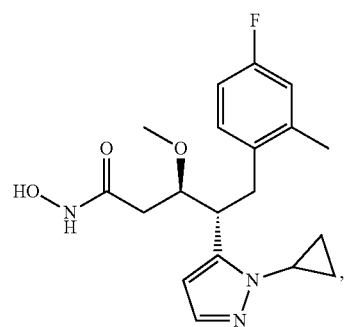
3-3
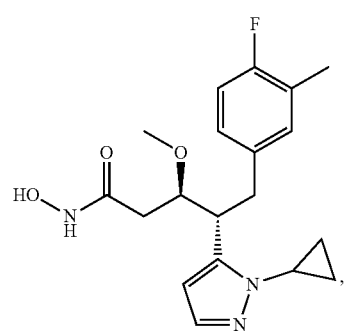
3-4
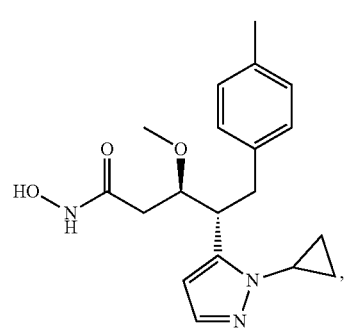
3-5
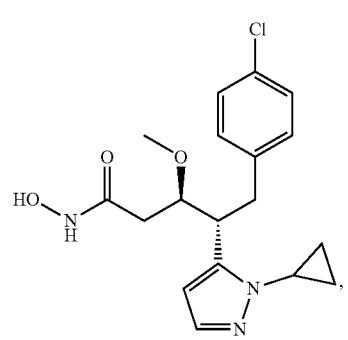
3-6
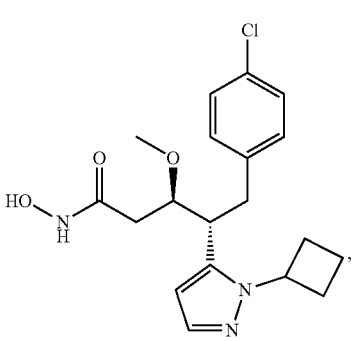
3-7
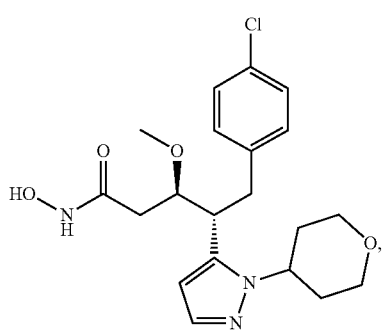
3-8
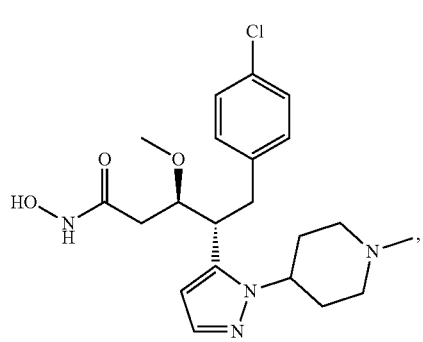
3-9
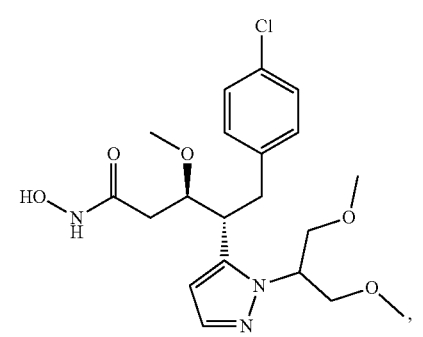
3-10
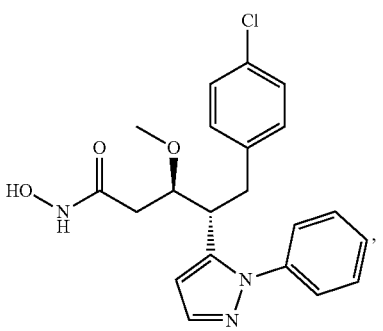

31. A compound of formula IV:

wherein
each R² is independently selected from the group consisting of hydrogen, halogen, and alkyl;
R³ is selected from the group consisting of hydrogen, alkyl, cycloalkyl aryl, hydroxyalkyl, alkoxyalkyl, aryloxyalkyl, aralkyloxyalkyl, aralkyl, alkylaminoalkyl, dialkylaminoalkyl, aralkylaminoalkyl, and heterocycloalkyl;
R⁵ is methyl or ethyl;
each of R², R³, and R⁵ being independently optionally substituted with hydroxy, alkoxy, halogen, or alkyl; and
m is an integer from 0 to 5.

32. A pharmaceutical composition comprising a compound according to claim 1, along with a pharmaceutically acceptable carrier.

33. A method of treating a subject exposed to a *botulinum* toxin comprising:
administering to the subject a pharmaceutical composition comprising a compound according to claim 1.

* * * * *

SEQUENCE LISTING

```
<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Enzymatic Substrate
<220> FEATURE:
<221> NAME/KEY: SITE
<222> LOCATION: (1)..(1)
<223> OTHER INFORMATION: Xaa is Aminobenzoic acid
<220> FEATURE:
<221> NAME/KEY: SITE
<222> LOCATION: (3)..(3)
<223> OTHER INFORMATION: Xaa is (D)-Arginine
<220> FEATURE:
<221> NAME/KEY: SITE
<222> LOCATION: (14)..(14)
<223> OTHER INFORMATION: Xaa is Norleucine
<220> FEATURE:
<221> NAME/KEY: SITE
<222> LOCATION: (16)..(16)
<223> OTHER INFORMATION: Xaa is 2,4-dinitrophenylhydrazine
      <

<400> SEQUENCE: 1

Xaa Thr Xaa Ile Asp Glu Ala Asn Gln Arg Ala Thr Lys Xaa Lys Xaa
1               5                   10                  15

<210> SEQ ID NO 2
<211> LENGTH: 440
<212> TYPE: PRT
<213> ORGANISM: Artificial Sequence
<220> FEATURE:
<223> OTHER INFORMATION: Enzyme for Assay
```

<400> SEQUENCE: 2

```
Met Arg His His His His His Gly Ala Gln Met Pro Phe Val Asn
1               5                   10                  15

Lys Gln Phe Asn Tyr Lys Asp Pro Val Asn Gly Val Asp Ile Ala Tyr
            20                  25                  30

Ile Lys Ile Pro Asn Ala Gly Gln Met Gln Pro Val Lys Ala Phe Lys
            35                  40                  45

Ile His Asn Lys Ile Trp Val Ile Pro Glu Arg Asp Thr Phe Thr Asn
    50                  55                  60

Pro Glu Glu Gly Asp Leu Asn Pro Pro Glu Ala Lys Gln Val Pro
65                  70                  75                  80

Val Ser Tyr Tyr Asp Ser Thr Tyr Leu Ser Thr Asp Asn Glu Lys Asp
                85                  90                  95

Asn Tyr Leu Lys Gly Val Thr Lys Leu Phe Glu Arg Ile Tyr Ser Thr
            100                 105                 110

Asp Leu Gly Arg Met Leu Leu Thr Ser Ile Val Arg Gly Ile Pro Phe
            115                 120                 125

Trp Gly Gly Ser Thr Ile Asp Thr Glu Leu Lys Val Ile Asp Thr Asn
    130                 135                 140

Cys Ile Asn Val Ile Gln Pro Asp Gly Ser Tyr Arg Ser Glu Glu Leu
145                 150                 155                 160

Asn Leu Val Ile Ile Gly Pro Ser Ala Asp Ile Ile Gln Phe Glu Cys
                165                 170                 175

Lys Ser Phe Gly His Glu Val Leu Asn Leu Thr Arg Asn Gly Tyr Gly
            180                 185                 190

Ser Thr Gln Tyr Ile Arg Phe Ser Pro Asp Phe Thr Phe Gly Phe Glu
        195                 200                 205

Glu Ser Leu Glu Val Asp Thr Asn Pro Leu Leu Gly Ala Gly Lys Phe
    210                 215                 220

Ala Thr Asp Pro Ala Val Thr Leu Ala His Glu Leu Ile His Ala Gly
225                 230                 235                 240

His Arg Leu Tyr Gly Ile Ala Ile Asn Pro Asn Arg Val Phe Lys Val
                245                 250                 255

Asn Thr Asn Ala Tyr Tyr Glu Met Ser Gly Leu Glu Val Ser Phe Glu
            260                 265                 270

Glu Leu Arg Thr Phe Gly Gly His Asp Ala Lys Phe Ile Asp Ser Leu
        275                 280                 285

Gln Glu Asn Glu Phe Arg Leu Tyr Tyr Tyr Asn Lys Phe Lys Asp Ile
    290                 295                 300

Ala Ser Thr Leu Asn Lys Ala Lys Ser Ile Val Gly Thr Thr Ala Ser
305                 310                 315                 320

Leu Gln Tyr Met Lys Asn Val Phe Lys Glu Lys Tyr Leu Leu Ser Glu
                325                 330                 335

Asp Thr Ser Gly Lys Phe Ser Val Asp Lys Leu Lys Phe Asp Lys Leu
            340                 345                 350

Tyr Lys Met Leu Thr Glu Ile Tyr Thr Glu Asp Asn Phe Val Lys Phe
        355                 360                 365

Phe Lys Val Leu Asn Arg Lys Thr Tyr Leu Asn Phe Asp Lys Ala Val
    370                 375                 380

Phe Lys Ile Asn Ile Val Pro Lys Val Asn Tyr Thr Ile Tyr Asp Gly
385                 390                 395                 400

Phe Asn Leu Arg Asn Thr Asn Leu Ala Ala Asn Phe Asn Gly Gln Asn
                405                 410                 415
```

```
Thr Glu Ile Asn Asn Met Asn Phe Thr Lys Leu Lys Asn Phe Thr Gly
            420             425             430

Leu Phe Glu Phe Tyr Lys Leu Leu
        435             440
```